Figure 3A:
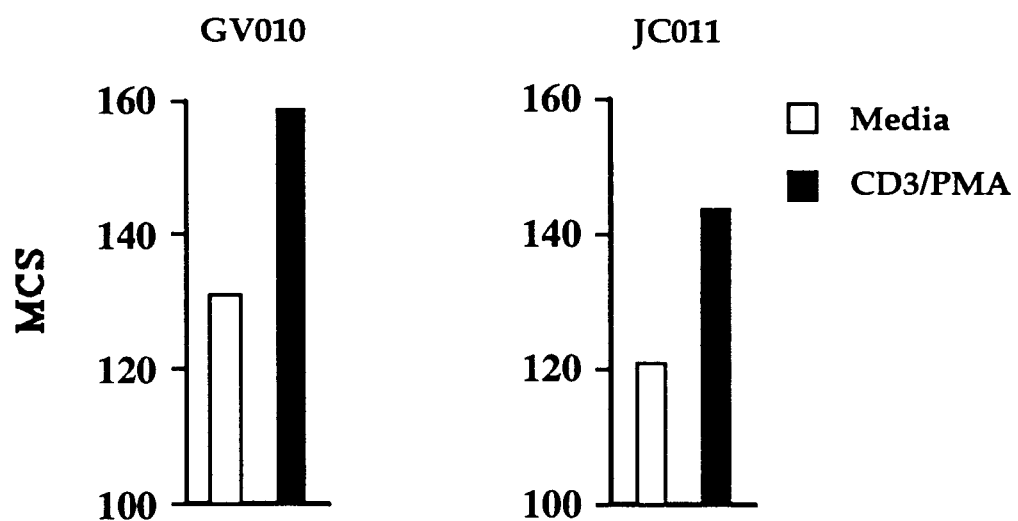

United States Patent [19]
Tam

[11] Patent Number: 5,932,556
[45] Date of Patent: Aug. 3, 1999

[54] METHODS AND COMPOSITIONS FOR REGULATION OF CD28 EXPRESSION

[76] Inventor: Robert C Tam, 1112 D Buckingham Dr., Costa Mesa, Calif. 92626

[21] Appl. No.: 08/529,878

[22] Filed: Sep. 18, 1995

[51] Int. Cl.[6] ............................. A61K 48/00; C12N 15/11
[52] U.S. Cl. ................................ 514/44; 536/24.5; 435/6; 435/375
[58] Field of Search ........................... 514/44; 435/320.1, 435/69.1, 172.3, 375; 935/34, 62, 71, 70, 72, 65; 536/24.5, 23.1, 23.5

[56] References Cited

PUBLICATIONS

Rojanasakul Y. "Antisense oligonucleotide therapeutics: drug delivery and targeting," Adv. Drug Deliery Rev., vol. 18: 115–131, 1996.
Miller et al. "Gene Transfer and Antisense Nucleic Acid Techniques," Parasitology Today, vol. 10: 92–97, Mar. 1994.
Wu Pong S. "Oligonucleotides: Opportunities for Drug Therapy and Research," Pharaceutical Technology, vol. 18: 102–114, Oct. 1994.
Stull et al. "Antigene, Ribozyme and Aptamer Nucleic Acid Drugs: Progress and Prospects," Pharmaceutical Research, vol. 12: 465–483, Apr. 1995.
Wagner et al. "Gene inhibition using antisense oligodeoxynucleotides," Nature, vol. 372: 333–335, Nov. 1994.
Stein et al. "Antisense Oligonucleotides as Therapeutic Agents–Is the Bullet Really Majical?," Science, vol. 261: 1004–1012, Aug. 1993.
Weiss et al. "Upping the Antisense Ante," Science News, vol. 139: 108–109, 1991.
Gross et al. "The murine homologue of the T lymphocyte antigen CD28," J. of Immunology, vol. 144, No. 8, pp. 3201–3210, 1990.
Aruffo et al. "Molecular cloning of a CD28 cDNA by a high–efficiency COS expression system," vol. 84, No. 23: 8573–8577, 1987.
Uhlmann et al. "Antisense Oligonucleotides: A New Therpeutic Principle," Chemical Reviews, vol. 90, No. 4: 543–584, 1990.
Schultz et al. "Refined solution structure of the dimeric quadruplex formed from the Oxytricha telomeric oligonucleotide d(GGGGTTTTGGGG)," vol. 2, No. 3: 10718–10724, Mar. 1994.
Eck et al. "Gene–Based Therapy," Gooman & Gilman's The Pharmacological Basis of Therapeutics, Ninth Edition, McGraw–Hill, New York, Chapter 5, 1995.
Bennett, C. F., Chiang, M. Y., Wilson–Lingardo, L., Wyatt, J. R. (1994) *Nucleic Acids Res.* 22, 3202–3209.
Burgess, T. L., Fisher, E. F., Ross, S. L., Bready, J. V., Qian, Y.–X., Bayewitch, L. A., Cohen, A. M., Herrera, C. J., Hu, S. S.–F., Kramer, T. B., Lott, F. D., Martin, F. H., Pierce, G. F., Simonet, L., Farrell, C. L. (1995) *Proc. Natl. Acad. Sci. USA* 92, 4051–4055).

*Primary Examiner*—James Martinell
*Assistant Examiner*—Karen M. Hauda
*Attorney, Agent, or Firm*—Robert D. Fish; Crockett & Fish

[57] ABSTRACT

Methods and compositions are provided for the treatment of immune system-mediated diseases. The compositions of the invention have the property of reducing the expression of CD28 in cells of interest so as to moderate the pathogenic effects on the immune system in an immune system-mediated disease. The compositions of the invention include one or more different oligomers capable of reducing the expression of CD28. One aspect of the invention provides oligomers capable of reducing the expression of CD28 by interfering with its expression. The oligomers may be DNA, RNA, or various analogs thereof, and may include 14–50 base phosphorothioates having at least two sequences of GGGG separated by 3 to 5 bases. Other aspects of the invention provide genetic engineering vectors for the intracellular expression of oligomers of the invention in cells of interest, and formulations comprising one or more different oligomers of the invention. The formulations may be adapted for various forms of administration to the body or administration to cells to be reintroduced into the body. The methods of the invention involve modulating CD28 expression through the use of the oligomers of the invention. The methods may be used to treat immune system-mediated diseases and include methods of treating autoimmune disease, methods of reducing an inflammation response, methods of reducing the production of selected cytokines, methods of inactivating T cells, and methods of immunosuppressing a transplant patient.

6 Claims, 18 Drawing Sheets

Figure 1A

```
CCCTTTCCTT TTTCTCTCT CCCCTTCCTT CCTTCTTTCC TTCTTTTCTT      -661
TTCTTTTCTT TTCTTTCTCT CTTTCTTTCT GTCTTTCTTT TCTCATTCTG      -611
TTGCCCTGGC TGGAGTGCAG TGGCATGATC TCGGCTCATA GCAGCCTCCA      -561
CCTCCTGGGT TCAAGCGATT CTCCTGCCTT AGCCCTCCCT AGTAGCTGGA      -511
TTACAGGTAC CCACCATGAT GCCTGGCTAA TTTTTTGTAT TTTCAATGGA      -461
GACGGGGTTT CACCATGTTG GCCAGGCTCG TCTTGACCTC CTGGCCTCAA      -411
ATGATCCACC CACTTTGGCC TCCCAAATTG CTGGCATTAC AGGCGTGAGC      -361
CACTGCACCC GGCCTGTTCC TTCTTAAGAA CACTTTGTCT CCCCTTTAAT      -311
CTCTGCTGGA TTTCAAGCAC CCCTTTTACA CAACTCTTGA TATCCATCAA      -261
TAAAGAATAA TTCCCATAAG CCCATCATGT AGTGACCGAC TATTTTTCAG      -211
TGACAAAAAA AAAGTCTTTA AAAATAGAAG TAAAAGTCTA AAGTCATCAA      -161
AACAACGTTA TATCCTGTGT GAAATGCTGC AGTCAGGATG CCTTGTGGTT      -111
TGAGTGCCTT GATCATGTGC CCTAAGGGGA TGGTGGCGGT GGTGGTGGCC      -61
GTGGATGACG G                                                -11
```

Figure 1B

```
AGACTCTCAG GCCTTGGCAG GTGCGTCTTT CAGTTCCCCT CACACTTCGG      50
GTTCCTCGGG GAGGAGGGGC TGGAACCCTA GCCCATCGTC AGGACAAAGA      100
                                                  M
TGCTCAGGCT GCTCTTGGCT CTCAACTTAT TCCCTTCAAT TCAAGTAACA      150
etLeuArgLe uLeuLeuAla LeuAsnLeuP heProSerIl eGlnValThr
GGAAACAAGA TTTTGGTGAA GCAGTCGCCC ATGCTTGTAG CGTACGACAA      200
GlyAsnLysI leLeuValLy sGlnSerPro MetLeuValA laTyrAspAs
TGCGGTCAAC CTTAGCTGCA AGTATTCCTA CAATCTCTTC TCAAGGGAGT      250
nAlaValAsn LeuSerCysL ysTyrSerTy rAsnLeuPhe SerArgGluP
TCCGGGCATC CCTTCACAAA GGACTGGATA GTGCTGTGGA AGTCTGTGTT      300
heArgAlaSe rLeuHisLys GlyLeuAspS erAlaValGl uValCysVal
GTATATGGGA ATTACTCCCA GCAGCTTCAG GTTTACTCAA AAACGGGTT      350
ValTyrGlyA snTyrSerGl nGlnLeuGln ValTyrSerL ysThrGlyPh
CAACTGTGAT GGGAAATTGG GCAATGAATC AGTGACATTC TACCTCCAGA      400
eAsnCysAsp GlyLysLeuG lyAsnGluSe rValThrPhe TyrLeuGlnA
ATTTGTATGT TAACCAAACA GATATTTACT TCTGCAAAAT TGAAGTTATG      450
snLeuTyrVa lAsnGlnThr AspIleTyrP heCysLysIl eGluValMet
```

Figure 1C

| | |
|---|---|
| TATCCTCCTC CTTACCTAGA CAATGAGAAG AGCAATGGAA CCATTATCCA<br>TyrProProP roTyrLeuAs pAsnGluLys SerAsnGlyT hrIleIleHi | 500 |
| TGTGAAAGGG AAACACCTTT GTCCAAGTCC CCTATTTCCC GGACCTTCTA<br>sValLysGly LysHisLeuC ysProSerPr oLeuPhePro GlyProSerL | 550 |
| AGCCCTTTTG GGTGCTGGTG GTGGTTGGTG GAGTCCTGGC TTGCTATAGC<br>ysProPheTr pValLeuVal ValValGlyG lyValLeuAl aCysTyrSer | 600 |
| TTGCTAGTAA CAGTGGCCTT TATTATTTTC TGGGTGAGGA GTAAGAGGAG<br>LeuLeuValT hrValAlaPh eIleIlePhe TrpValArgS erLysArgSe | 650 |
| CAGGCTCCTG CACAGTGACT ACATGAACAT GACTCCCCGC CGCCCCGGGC<br>rArgLeuLeu HisSerAspT yrMetAsnMe tThrProArg ArgProGlyP | 700 |
| CCACCCGCAA GCATTACCAG CCCTATGCCC CACCACGCGA CTTCGCAGCC<br>roThrArgLy sHisTyrGln ProTyrAlaP roProArgAs pPheAlaAla | 750 |
| TATCGCTCCT GACACGGACG CCTATCCAGA AGCCAGCCGG CTGGCAGCCC<br>TyrArgSer. .. | 800 |
| CCATCTGCTC AATATCACTG CTCTGGATAG GAAATGACCG CCATCTCCAG | 850 |
| CCGGCCACCT CAGCCCCTGT TGGGCCACCA ATGCCAATTT TTCTCGAGTG | 900 |
| ACTAGACCAA ATATCAAGAT CATTTTGAGA CTCTGAAATG AAGTAAAAGA | 950 |
| GATTTCCTGT GACAGGCCAA GTCTTACAGT GCCATGGCCC ACATTCCAAC | 1000 |
| TTACCATGTA CTTAGTGACT TGACTGAGAA GTTAGGGTAG AAAACAAAAA | 1050 |
| GGGAGTGGAT TCTGGGAGCC TCTTCCCTTT CTCACTCACC TGCACATCTC | 1100 |
| AGTCAAGCAA AGTGTGGTAT CCACAGACAT TTTAGTTGCA GAAGAAAGGC | 1150 |
| TAGGAAATCA TTCCTTTTGG TTAAATGGGT GTTTAATCTT TTGGTTAGTG | 1200 |
| GGTTAAACGG GGTAAGTTAG AGTAGGGGGA GGGATAGGAA GACATATTTA | 1250 |
| AAAACCATTA AAACACTGTC TCCCACTCAT GAAATGAGCC ACGTAGTTCC | 1300 |
| TATTTAATGC TGTTTTCCTT TAGTTTAGAA ATACATAGAC ATTGTCTTTT | 1350 |
| ATGAATTCTG ATCATATTTA GTCATTTTGA CCAAATGAGG GATTTGGTCA | 1400 |
| AATGAGGGAT TCCCTCAAAG CAATATCAGG TAAACCAAGT TGCTTTCCTC | 1450 |
| ACTCCCTGTC ATGAGACTTC AGTGTTAATG TTCACAATAT ACTTTCGAAA | 1500 |
| GAATAAAATA GTTC | 1514 |

Figure 2
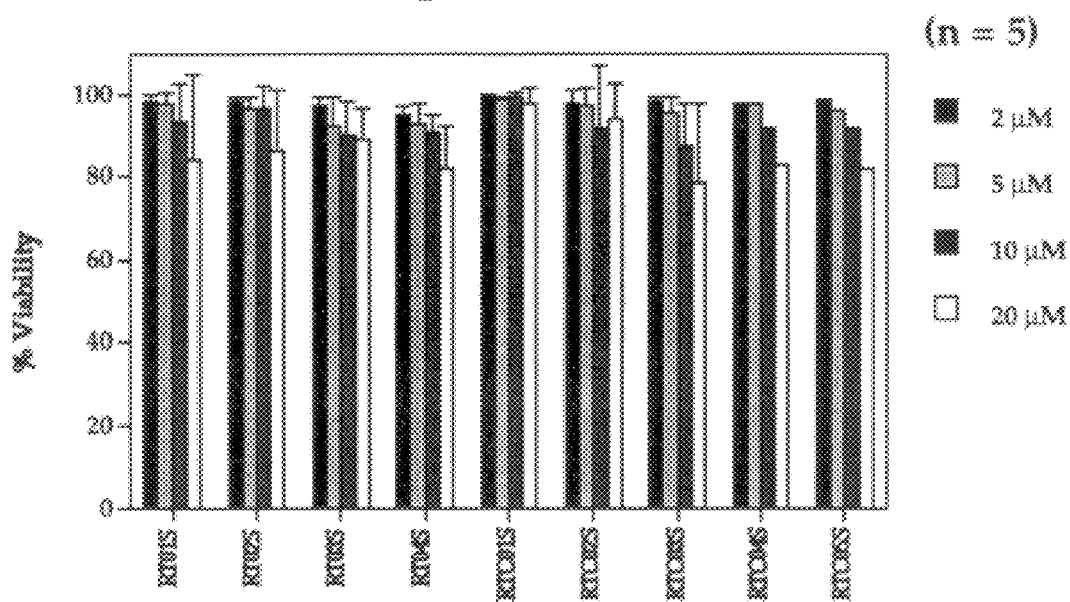
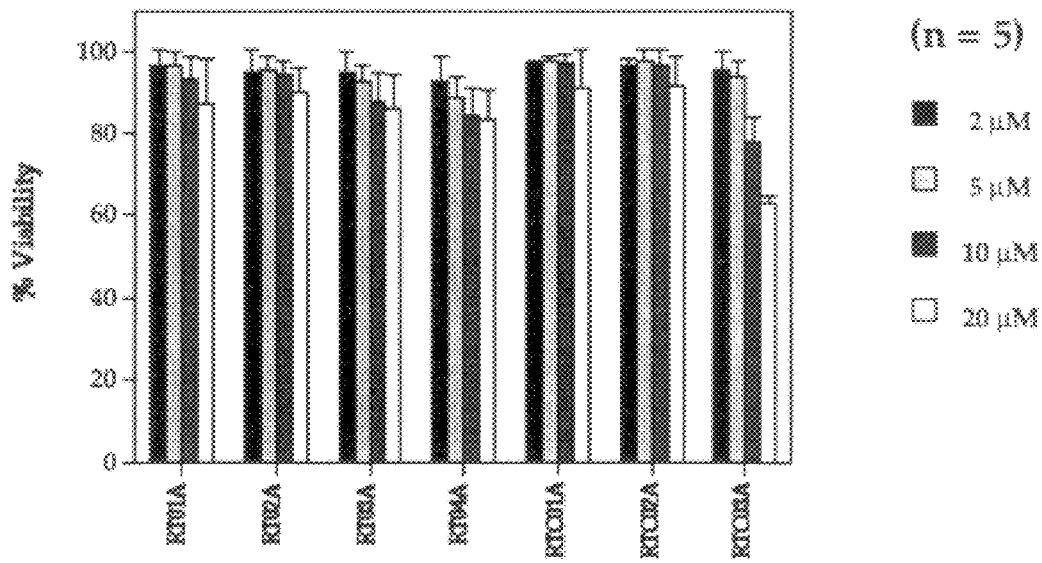

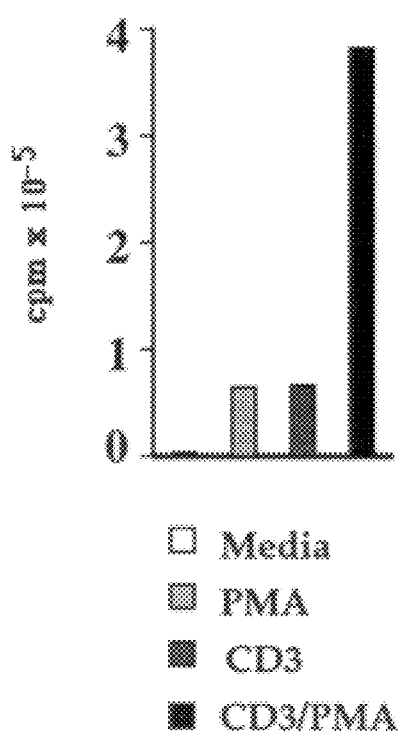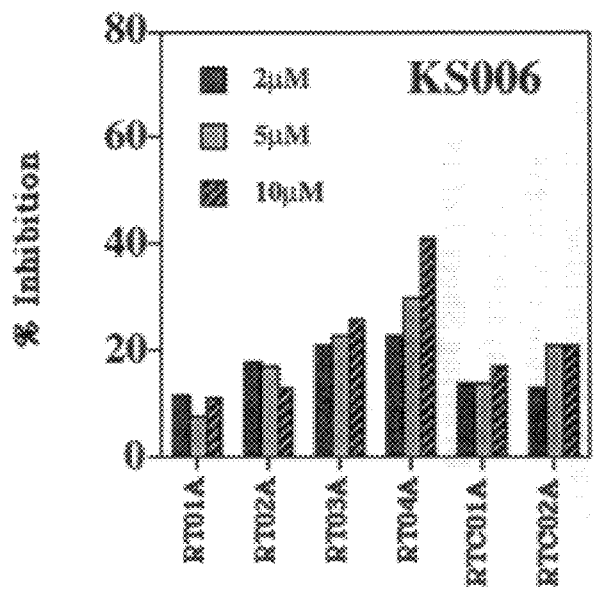
Figure 4A
Figure 4B

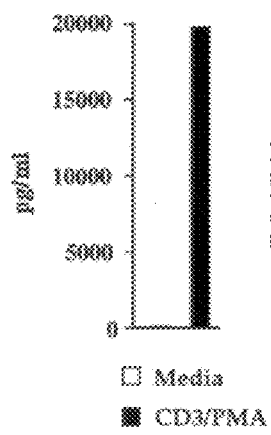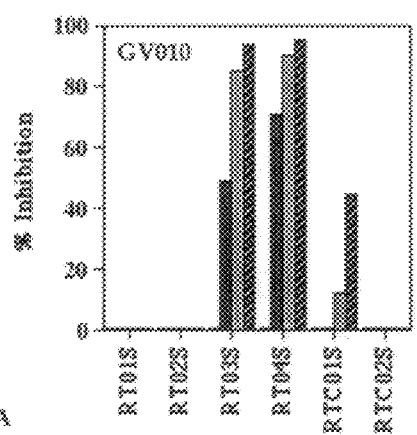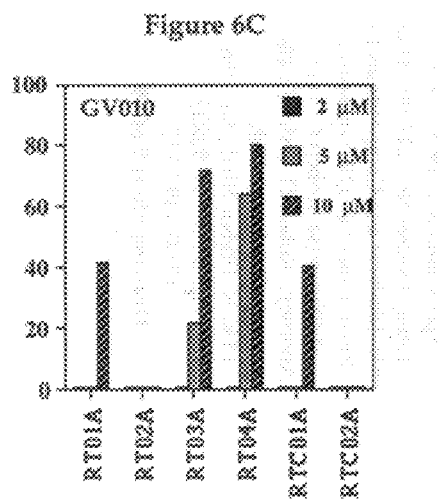

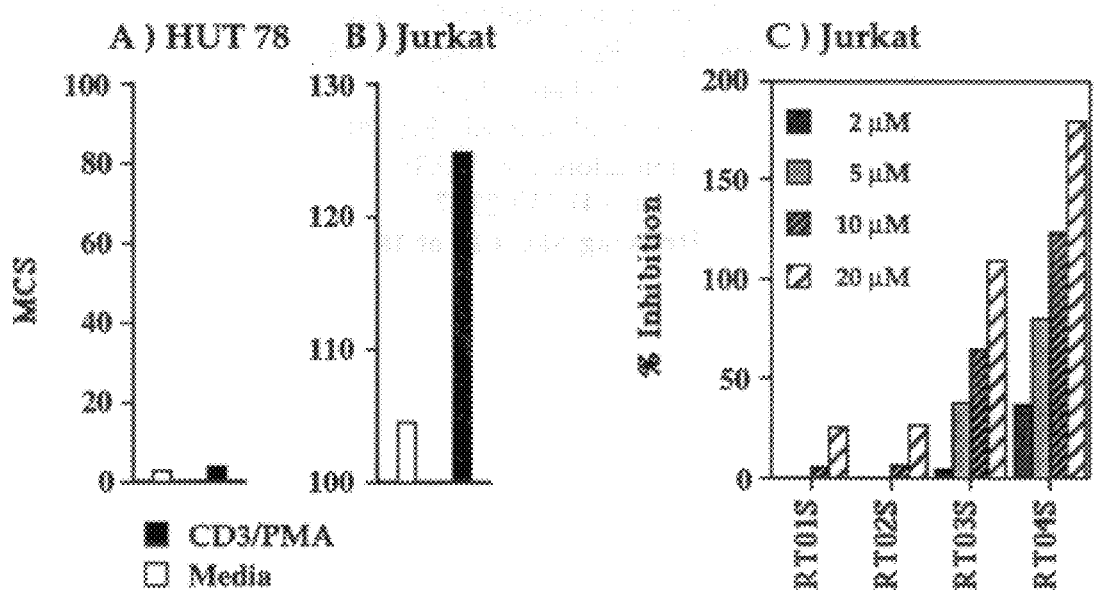

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
      (A) LENGTH: 19 base pairs

```
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:1:

TTGTCCTGAC GATGGGCTA                                                 19

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

AGCAGCCTGA GCATCTTTGT                                                20

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

TTGGAGGGGG TGGTGGGG                                                  18

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

GGGTTGGAGG GGGTGGTGGG G                                              21

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

TAGCCCATCG TCAGGACAA                                                 19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)
```

(xi) SEQUENCE DESCRIPTION: SEQ ID NO:6:

ACAAAGATGC TCAGGCTGCT                                              20

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

CTCCAGCCAA TCGGAAGGCT CTTTAA                                       26

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

TTTTGGTTGG TGTGGTTTGT G                                            21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

GTGTGTGTGT GTGTGTGTGT G                                            21

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:10:

AACCTCCCCC ACCACCCC                                                18

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:11:

AGTTGAGAGC CAAGAGCAGC                                              20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:12:

GCTAAGGTTG ACCGCATTGT                                                   20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:13:

AGTCCTTTGT GAAGGGATGC                                                   20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:14:

ACCTGAAGCT GCTGGGAGTA                                                   20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:15:

CCCAATTTCC CATCACAGTT                                                   20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:16:

GCAAGCTATA GCAAGCCAGG   20

(2) INFORMATION FOR SEQ ID NO:17:

(i) SEQUENCE CHARACTERISTICS:
        (A) LENGTH: 20 base pairs (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:17:

CAGGAGCCTG CTCCTCTTAC                                                   20

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:18:

GTGTCAGGAG CGATAGGCTG                                                   20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:19:

GGCCTGTCAC AGGAAATCTC                                                   20

(2) INFORMATION FOR SEQ ID NO:20:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:20:

AGCCGGCTGG CTTCTG                                                       16

(2) INFORMATION FOR SEQ ID NO:21:

(i) SEQUENCE CHARACTERISTICS:
            (A) LENGTH: 19 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:21:

AAATTGGCAT TGGTGGGCC                                                    19

(2) INFORMATION FOR SEQ ID NO:22:

(i) SEQUENCE CHARACTERISTICS:
            (A) LENGTH: 20 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:22:

TAAGTTGGAA TGTGGGCCAT                                                      20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:23:

CTCCCAGAAT CCACTCCCTT                                                      20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:24:

GCTTGACTGA GATGTGCAGG                                                      20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:25:

TCCTAGCCTT TCTTCTGCAA                                                      20

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:26:

CGTACGCTAC AAGCATGGG                                                       19

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:27:

TGAGAAAGGG AAGAGGCTCC                                                      20

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:28:

GAAGTCGCGT GGTGGG                                           16

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:29:

AAATTAGCCA GGCATCATGG                                    20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:30:

AGTGGGTGGA TCATTTGAGG                                    20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:31:

TGCTTGAAAT CCAGCAGAGA                                    20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:32:

CATGATGGGC TTATGGGAAT                                    20

(2) INFORMATION FOR SEQ ID NO:33:

(i) SEQUENCE CHARACTERISTICS:
        (A) LENGTH: 18 base pairs

```
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:33:

CAGTGGCTCA CGCCTGTA                                                   18

(2) INFORMATION FOR SEQ ID NO:34:

(i) SEQUENCE CHARACTERISTICS:
          (A) LENGTH: 20 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:34:

GGGGTTGGTT GGTTGTTTGG                                                 20

(2) INFORMATION FOR SEQ ID NO:35:

(i) SEQUENCE CHARACTERISTICS:
          (A) LENGTH: 17 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:35:

GTGTTTGTGT GGGGTTT                                                    17

(2) INFORMATION FOR SEQ ID NO:36:

(i) SEQUENCE CHARACTERISTICS:
          (A) LENGTH: 17 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:36:

GGGGTTTTTT GTGTGGT                                                    17

(2) INFORMATION FOR SEQ ID NO:37:

(i) SEQUENCE CHARACTERISTICS:
          (A) LENGTH: 661 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:37:

CCCTTTCCTT TTTTCTCTCT CCCCTTCCTT CCTTCTTTCC TTCTTTTCTT                 50

TTCTTTTCTT TTCTTTCTCT CTTTCTTTCT GTCTTTCTTT TCTCATTCTG                100

TTGCCCTGGC TGGAGTGCAG TGGCATGATC TCGGCTCATA GCAGCCTCCA                150

CCTCCTGGGT TCAAGCGATT CTCCTGCCTT AGCCCTCCCT AGTAGCTGGA                200

TTACAGGTAC CCACCATGAT GCCTGGCTAA TTTTTTGTAT TTTCAATGGA                250

GACGGGGTTT CACCATGTTG GCCAGGCTCG TCTTGACCTC CTGGCCTCAA                300
```

```
ATGATCCACC CACTTTGGCC TCCCAAATTG CTGGCATTAC AGGCGTGAGC        350

CACTGCACCC GGCCTGTTCC TTCTTAAGAA CACTTTGTCT CCCCTTTAAT        400

CTCTGCTGGA TTTCAAGCAC CCCTTTTACA CAACTCTTGA TATCCATCAA        450

TAAAGAATAA TTCCCATAAG CCCATCATGT AGTGACCGAC TATTTTTCAG        500

TGACAAAAAA AAAGTCTTTA AAAATAGAAG TAAAAGTCTA AAGTCATCAA        550

AACAACGTTA TATCCTGTGT GAAATGCTGC AGTCAGGATG CCTTGTGGTT        600

TGAGTGCCTT GATCATGTGC CCTAAGGGGA TGGTGGCGGT GGTGGTGGCC        650

GTGGATGACG G                                                  661

(2) INFORMATION FOR SEQ ID NO:38:

(i) SEQUENCE CHARACTERISTICS:
        (A) LENGTH: 450 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 100..450

(xi) SEQUENCE DESCRIPTION: SEQ ID NO:38:

AGACTCTCAG GCCTTGGCAG GTGCGTCTTT CAGTTCCCCT CACACTTCGG        50

GTTCCTCGGG GAGGAGGGGC TGGAACCCTA GCCCATCGTC AGGACAAAG         99

ATG CTC AGG CTG CTC TTG GCT CTC AAC TTA                       129
Met Leu Arg Leu Leu Leu Ala Leu Asn Leu
            5                  10

TTC CCT TCA ATT CAA GTA ACA GGA AAC AAG                       159
Phe Pro Ser Ile Gln Val Thr Gly Asn Lys
            15                 20

ATT TTG GTG AAG CAG TCG CCC ATG CTT GTA                       189
Ile Leu Val Lys Gln Ser Pro Met Leu Val
            25                 30

GCG TAC GAC AAT GCG GTC AAC CTT AGC TGC                       219
Ala Tyr Asp Asn Ala Val Asn Leu Ser Cys
            35                 40

AAG TAT TCC TAC AAT CTC TTC TCA AGG GAG                       249
Lys Tyr Ser Tyr Asn Leu Phe Ser Arg Glu
            45                 50

TTC CGG GCA TCC CTT CAC AAA GGA CTG GAT                       279
Phe Arg Ala Ser Leu His Lys Gly Leu Asp
            55                 60

AGT GCT GTG GAA GTC TGT GTT GTA TAT GGG                       309
Ser Ala Val Glu Val Cys Val Val Tyr Gly
            65                 70

AAT TAC TCC CAG CAG CTT CAG GTT TAC TCA                       339
Asn Tyr Ser Gln Gln Leu Gln Val Tyr Ser
            75                 80

AAA ACG GGG TTC AAC TGT GAT GGG AAA TTG                       369
Lys Thr Gly Phe Asn Cys Asp Gly Lys Leu
            85                 90

GGC AAT GAA TCA GTG ACA TTC TAC CTC CAG                       399
Gly Asn Glu Ser Val Thr Phe Tyr Leu Gln
            95                 100

AAT TTG TAT GTT AAC CAA ACA GAT ATT TAC                       429
Asn Leu Tyr Val Asn Gln Thr Asp Ile Tyr
            100                110
```

```
TTC TGC AAA ATT GAA GTT ATG                                              450
Phe Cys Lys Ile Glu Val Met
                115
```

(2) INFORMATION FOR SEQ ID NO:39:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:39:

```
Met Leu Arg Leu Leu Ala Leu Asn Leu
                5                 10

Phe Pro Ser Ile Gln Val Thr Gly Asn Lys
                15                    20

Ile Leu Val Lys Gln Ser Pro Met Leu Val
                25                    30

Ala Tyr Asp Asn Ala Val Asn Leu Ser Cys
                35                    40

Lys Tyr Ser Tyr Asn Leu Phe Ser Arg Glu
                45                    50

Phe Arg Ala Ser Leu His Lys Gly Leu Asp
                55                    60

Ser Ala Val Glu Val Cys Val Val Tyr Gly
                65                    70

Asn Tyr Ser Gln Gln Leu Gln Val Tyr Ser
                75                    80

Lys Thr Gly Phe Asn Cys Asp Gly Lys Leu
                85                    90

Gly Asn Glu Ser Val Thr Phe Tyr Leu Gln
                95                   100

Asn Leu Tyr Val Asn Gln Thr Asp Ile Tyr
                100                  110

Phe Cys Lys Ile Glu Val Met
                115
```

(2) INFORMATION FOR SEQ ID NO:40:

(i) SEQUENCE CHARACTERISTICS:
        (A) LENGTH: 1064 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..309

(xi) SEQUENCE DESCRIPTION: SEQ ID NO:40:

```
TAT CCT CCT CCT TAC CTA GAC AAT GAG AAG                                  30
Tyr Pro Pro Pro Tyr Leu Asp Asn Glu Lys
                120                  125

AGC AAT GGA ACC ATT ATC CAT GTG AAA GGG                                  60
Ser Asn Gly Thr Ile Ile His Val Lys Gly
                130                  135

AAA CAC CTT TGT CCA AGT CCC CTA TTT CCC                                  90
Lys His Leu Cys Pro Ser Pro Leu Phe Pro
```

```
              140                 145
GGA CCT TCT AAG CCC TTT TGG GTG CTG GTG                      120
Gly Pro Ser Lys Pro Phe Trp Val Leu Val
          150                 155

GTG GTT GGT GGA GTC CTG GCT TGC TAT AGC                      150
Val Val Gly Gly Val Leu Ala Cys Tyr Ser
          160                 165

TTG CTA GTA ACA GTG GCC TTT ATT ATT TTC                      180
Leu Leu Val Thr Val Ala Phe Ile Ile Phe
          170                 175

TGG GTG AGG AGT AAG AGG AGC AGG CTC CTG                      210
Trp Val Arg Ser Lys Arg Ser Arg Leu Leu
          180                 185

CAC AGT GAC TAC ATG AAC ATG ACT CCC CGC                      240
His Ser Asp Tyr Met Asn Met Thr Pro Arg
          190                 195

CGC CCC GGG CCC ACC CGC AAG CAT TAC CAG                      270
Arg Pro Gly Pro Thr Arg Lys His Tyr Gln
          200                 205

CCC TAT GCC CCA CCA CGC GAC TTC GCA GCC                      300
Pro Tyr Ala Pro Pro Arg Asp Phe Ala Ala
          210                 215

TAT CGC TCC                                                  309
Tyr Arg Ser
    220

TGACACGGAC GCCTATCCAG AAGCCAGCCG GCTGGCAGCC CCCATCTGCT        359

CAATATCACT GCTCTGGATA GGAAATGACC GCCATCTCCA GCCGGCCACC        409

TCAGCCCCTG TTGGGCCACC AATGCCAATT TTTCTCGAGT GACTAGACCA        459

AATATCAAGA TCATTTTGAG ACTCTGAAAT GAAGTAAAAG AGATTTCCTG        509

TGACAGGCCA AGTCTTACAG TGCCATGGCC CACATTCCAA CTTACCATGT        559

ACTTAGTGAC TTGACTGAGA AGTTAGGGTA GAAAACAAAA AGGGAGTGGA        609

TTCTGGGAGC CTCTTCCCTT TCTCACTCAC CTGCACATCT CAGTCAAGCA        659

AAGTGTGGTA TCCACAGACA TTTTAGTTGC AGAAGAAAGG CTAGGAAATC        709

ATTCCTTTTG GTTAAATGGG TGTTTAATCT TTTGGTTAGT GGGTTAAACG        759

GGGTAAGTTA GAGTAGGGGG AGGGATAGGA AGACATATTT AAAAACCATT        809

AAAACACTGT CTCCCACTCA TGAAATGAGC CACGTAGTTC CTATTTAATG        859

CTGTTTTCCT TTAGTTTAGA AATACATAGA CATTGTCTTT TATGAATTCT        909

GATCATATTT AGTCATTTTG ACCAAATGAG GGATTTGGTC AAATGAGGGA        959

TTCCCTCAAA GCAATATCAG GTAAACCAAG TTGCTTTCCT CACTCCCTGT       1009

CATGAGACTT CAGTGTTAAT GTTCACAATA TACTTTCGAA AGAATAAAAT       1059

AGTTC                                                       1064

(2) INFORMATION FOR SEQ ID NO:41:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO:41:

Tyr Pro Pro Pro Tyr Leu Asp Asn Glu Lys
              5                 10
```

```
Ser Asn Gly Thr Ile Ile His Val Lys Gly
             15                   20

Lys His Leu Cys Pro Ser Pro Leu Phe Pro
             25                   30

Gly Pro Ser Lys Pro Phe Trp Val Leu Val
             35                   40

Val Val Gly Gly Val Leu Ala Cys Tyr Ser
             45                   50

Leu Leu Val Thr Val Ala Phe Ile Ile Phe
             55                   60

Trp Val Arg Ser Lys Arg Ser Arg Leu Leu
             65                   70

His Ser Asp Tyr Met Asn Met Thr Pro Arg
             75                   80

Arg Pro Gly Pro Thr Arg Lys His Tyr Gln
             85                   90

Pro Tyr Ala Pro Pro Arg Asp Phe Ala Ala
             95                  100

Tyr Arg Ser (2) INFORMATION FOR SEQ ID NO:42:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:42:

TTGTGGTGAC GATGGGCTA                                                    19

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:43:

AGCAGCCTGA GCATCTTTGT                                                   20

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:44:

TTGGAGGGGG TGGTGGGG                                                     18

(2) INFORMATION FOR SEQ ID NO:45:

(i) SEQUENCE CHARACTERISTICS:
        (A) LENGTH: 21 base pairs
```

```
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:45:

GGGTTGGAGG GGGTGGTGGG G                                              21

(2) INFORMATION FOR SEQ ID NO:46:

(i) SEQUENCE CHARACTERISTICS:
            (A) LENGTH: 19 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:46:

TAGCCCATCG TCAGGACAA                                                 19

(2) INFORMATION FOR SEQ ID NO:47:

(i) SEQUENCE CHARACTERISTICS:
            (A) LENGTH: 20 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:47:

ACAAAGATGC TCAGGCTGCT                                                20

(2) INFORMATION FOR SEQ ID NO:48:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:48:

AACCTCCCCC ACCACCCC                                                  18
```

METHODS AND COMPOSITIONS FOR REGULATION OF CD28 EXPRESSION

I. FIELD OF THE INVENTION

The invention is in the field of modulating gene expression through the use of oligomers, particularly those oligomers effective in treating immune system-mediated diseases.

II. BACKGROUND OF THE INVENTION

While the immune system plays a crucial role in protecting higher organisms against life-threatening infections, the immune system also plays a crucial part in the pathogenesis of numerous diseases. Those diseases in which the immune system plays a part include autoimmune diseases in which the immune system reacts against an autologous antigen, e.g., systemic lupus erythematosus, or diseases associated with immunoregulation initiated by reaction to a foreign antigen, e.g., graft vs. host disease observed in transplantation rejection.

The pathogenesis and exacerbation of many common T-cell mediated diseases result from an inappropriate immune response driven by abnormal T-cell activation. The presence of activated T-cells have been reported in many T-cell mediated skin diseases (Simon et al., (1994) *J. Invest Derm.*, 103:539–543). For example, psoriasis, which afflicts 2% of the Western population including four million Americans, is a skin disorder characterized by keratinocyte hyperproliferation and abnormal dermal and epidermal infiltration of activated T-cells. Many reports suggest a major role of these activated T-cells in the pathogenesis of psoriasis (Baadsgaard et al., (1990) *J. Invest Derm.*, 95:275–282, Chang et al., (1992) *Arch. Derm.*, 128:1479–1485, Schlaak et al., (1994) *J. Invest Derm.*, 102:145–149) and in AIDS-exacerbated psoriasis (Duvic (1990) *J. Invest. Derm.*, 90:38S–40S). In psoriasis, activated lesional T-cells predominantly release the Th1 cytokines (IL-2, interferon-gamma) (Schlaak et al., (1994) *J. Invest Derm.*, 102:145–149). These secreted cytokines induce normal keratinocytes to express the same phenotype (HLA DR+/ICAM-1+) as found in psoriasis lesions (Baadsgaard et al., (1990) *J. Invest Derm.*, 95:275–282). Also, by virtue of its in vitro and in vivo proinflammatory properties and because it is secreted in large amounts by both activated T-cells and keratinocytes from psoriatic lesions, IL-8 is considered to be a major contributor to the pathologic changes seen in psoriatic skin such as keratinocyte hyperproliferation. Furthermore, one of the B7 family of receptors (the natural ligands for CD28 found on activated APC), BB1, has been shown to be expressed in psoriatic but not unaffected skin keratinocytes (Nickoloff, et al., (1993) *Am. J. Pathology*, 142:1029–1040).

A number of other diseases are thought to be caused by aberrant T-cell activation, including Type I (insulin-dependent) diabetes mellitus, thyroiditis, sarcoidosis, multiple sclerosis, autoimmune uveitis, rheumatoid arthritis, systemic lupus erythematosus, inflammatory bowel disease (Crohn's and ulcerative colitis) and autoimmune hepatitis. In addition, a variety of syndromes including septic shock and tumor-induced cachexia may involve T-cell activation and augmented production of potentially toxic levels of lymphokines. Normal T-cell activation also mediates the rejection of transplanted cells and organs by providing the necessary signals for the effective destruction of the "foreign" donor tissue.

The activation of T-lymphocytes leading to T-cell proliferation and gene expression and secretion of specific immunomodulatory cytokines requires two independent signals. The first signal involves the recognition, by specific T-cell receptor/CD3 complex, of antigen presented by major histocompatibility complex molecules on the surface of antigen presenting cells (APCs). Antigen-nonspecific intercellular interactions between T-cells and APCs provide the second signal that serves to regulate T-cell responses to antigen. These secondary or costimulatory signals determine the magnitude of a T-cell response to antigen. Costimulated cells react by increasing the levels of specific cytokine gene transcription and by stabilizing selected mRNAs. In the absence of costimulation, T-cell activation results in an aborted or anergic T-cell response. One key costimulatory signal is provided by interaction of the T-cell surface receptor CD28 with B7-related molecules on APC (Linsley and Ledbetter (1993)*Ann. Rev. Immunol.*, 11:191–212). CD28 is constitutively expressed on 95% of CD4+ T-cells (which provide helper functions for B-cell antibody production) and 50% of CD8+ T-cells (which have cytotoxic functions) (Yamada et al., (1985) *Eur. J. Immunol.* 15:1164–1168). Following antigenic or in vitro mitogenic stimulation, further induction of surface levels of CD28 occurs, as well as the production of certain immunomodulatory cytokines. These include interleukin-2 (IL-2), required for cell cycle progression of T-cells, interferon-gamma, which displays a wide variety of anti-viral and anti-tumor effects and interleukin-8 (IL-8), known as a potent chemotactic factor for neutrophils and lymphocytes. These cytokines have been shown to be regulated by the CD28 pathway of T-cell activation (Fraser et al., (1991) *Science*, 251:313–316, Seder et al., (1994) *J. Exp. Med.*, 179:299–304, Wechsler et al., (1994) *J. Immunol.*, 153:2515–2523). IL-2, interferon-gamma, and IL-8 are essential in promoting a wide range of immune responses and have been shown to be overexpressed in many T-cell mediated disease states.

In some T-cell mediated skin disorders such as allergic contact dermatitis and lichen planus, CD28 was expressed in high levels in the majority of dermal and epidermal CD3+ T-cells but in normal skin and basal cell carcinoma (a non T-cell mediated skin disease), CD28 was expressed only in perivascular T-cells. Similarly, in both allergic contact dermatitis and lichen planus, B7 expression was found on dermal dendritic cells, dermal APCs and on keratinocytes but not in normal skin and basal cell carcinoma (Simon et al., (1994) *J. Invest Derm.*, 103:539–543). Therefore this suggests that the CD28/B7 pathway is an important mediator of T-cell-mediated skin diseases.

Aberrant T-cell activation associated with certain autoimmune diseases caused by the loss of self-tolerance is predominantly characterized by the presence of CD28+ T-cells and expression of its ligand, B7 on activated professional APCs (monocyte, macrophage or dendritic cells). These include autoimmune Graves thyroiditis (Garcia-Cozar et al., (1993) *Immunol.*, 12:32), sarcoidosis (Vandenbergh et al., (1993) *Int. Immunol.*, 5:317–321), rheumatoid arthritis (Verwilghen et al. (1994) *J. Immunol.*, 153:1378–1385) and systemic lupus erythematosus (Sfikakis et al., (1994) *Clin. Exp. Immunol.*, 96:8–14). In normal T-cell activation, which mediates the rejection of transplanted cells and organs, the binding of CD28 by its appropriate B7 ligand during T-cell receptor engagement is critical for proper allogeneic response to foreign antigens, for example, on donor tissue (Azuma et al., (1992) *J. Exp. Med.*, 175:353–360, Turka et al., (1992) *Proc. Nat. Acad. Sci. USA*, 89:11102–11105).

Traditional therapies for autoimmune diseases do not prevent T-cell activation; the effector step in the autoreactive immune responses to self-antigen. Drugs, such as steroids and non-steroid anti-inflammatory drugs (NSAIDS), are currently used to ameliorate symptoms, but they do not prevent the progression of the disease. In addition, steroids can have side effects such as inducing osteoporosis, organ toxicity and diabetes, and can accelerate the cartilage degeneration process and cause so-called post-injection flares for up to 2 to 8 hours. NSAIDS can have gastrointestinal side effects and increase the risk of agranulocytosis and iatrogenic hepatitis. Immunosuppressive drugs are also used as another form of therapy, especially in advanced disease stages. However, these drugs suppress the entire immune system and often treatment has severe side effects including hypertension and nephrotoxicity. Also established immunosuppressants such as cyclosporin and FK506 cannot inhibit the CD28-dependent T-cell activation pathway (June et al., (1987) *Mol. Cell. Biol.*, 7:4472–4481).

Given the shortcomings of currently-available pharmaceuticals and methods for treating immune system-mediated diseases, it is of interest to provide new methods and compositions for treating such diseases.

III. SUMMARY OF THE INVENTION

The subject invention provides methods and compositions for the treatment of immune system-mediated diseases. The compositions of the invention have the property of reducing the expression of CD28 in cells of interest, which in turn moderate pathogenic effects of the immune system in an immune system-mediated disease. The subject methods of reducing CD28 expression may also serve as methods of reducing the effects of antigenic stimulation of CD28$^+$ T cells, thereby decreasing the level of activation of CD28$^+$ T cells and the release of cytokines associated with T cell activation, including interleukin-2, interferon-gamma, and interleukin-8. The compositions of the invention include many different oligomers capable of reducing the expression of CD28.

One aspect of the invention is to provide oligomers capable of reducing the expression of CD28 by interfering with the expression of CD28. The oligomers of the invention have nucleic acid base sequence homology to a CD28 gene or a CD28 gene transcript, or a portion thereof, where the homology is sufficient to permit formation of a nucleic acid double-stranded helix or triple-stranded helix under intracellular conditions. The oligomers of the invention may be DNA, RNA, or various synthetic analogs thereof. In particular embodiments, oligomers having 11 to 50 bases comprising at least two sequences of GGGG separated by 3 to 5 bases.

Another aspect of the invention is to provide genetic engineering vectors for the intracellular expression of oligomers of the invention in cells of interest, preferably cells that naturally express CD28.

Another aspect of the invention is to provide pharmaceutical formulations comprising one or more different oligomers of the invention. The pharmaceutical formulations may be adapted for various forms of administration to the body or administration to cells to be reintroduced into the body.

Another aspect of the invention is to provide methods for the treatment of immune system-mediated diseases. The methods of the invention involve modulating CD28 expression by administering an effective amount of the oligomers of the invention. The methods of the invention include methods of treating autoimmune disease, methods of reducing inflammation, response, methods of reducing the production of selected cytokines, methods of inactivating T cells, and methods of immunosuppressing a transplant patient.

IV. BRIEF DESCRIPTION OF THE DRAWINGS

FIGS. 1A–C is the sequence of the 5' untranslated region of the CD28 gene and the mRNA sequence of human CD28 (1B, 1C). FIGS. 1B and 1C represent different contiguous portions of a polynucleotide sequence.

FIG. 2 is a graphical representation of the percentage of viable (live) T-cells following treatment with various CD28-specific and control phosphorothioate and phosphorothioate-3'hydroxypropylamine oligonucleotides.

Figure 3B:
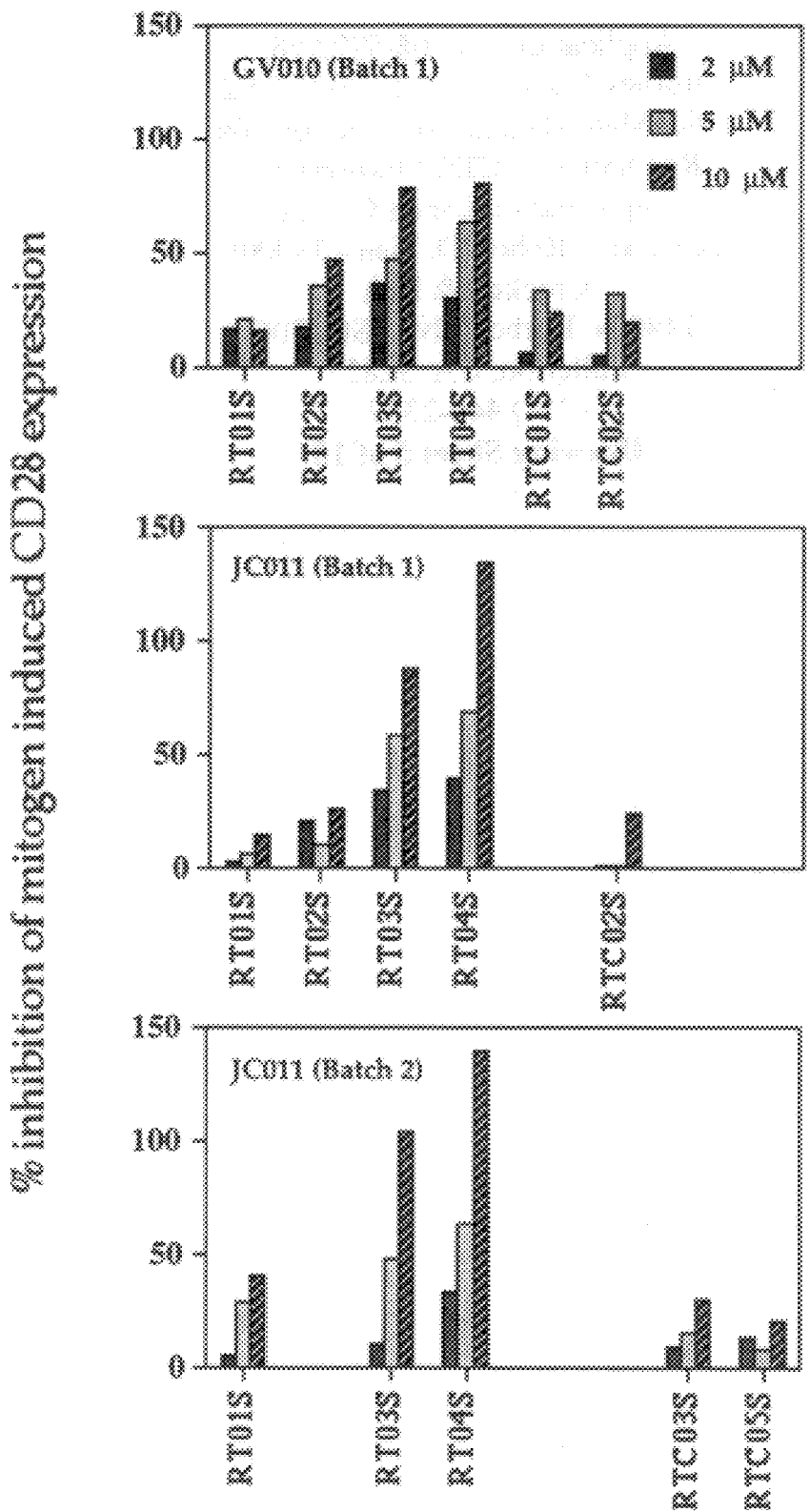
Figure 3C:
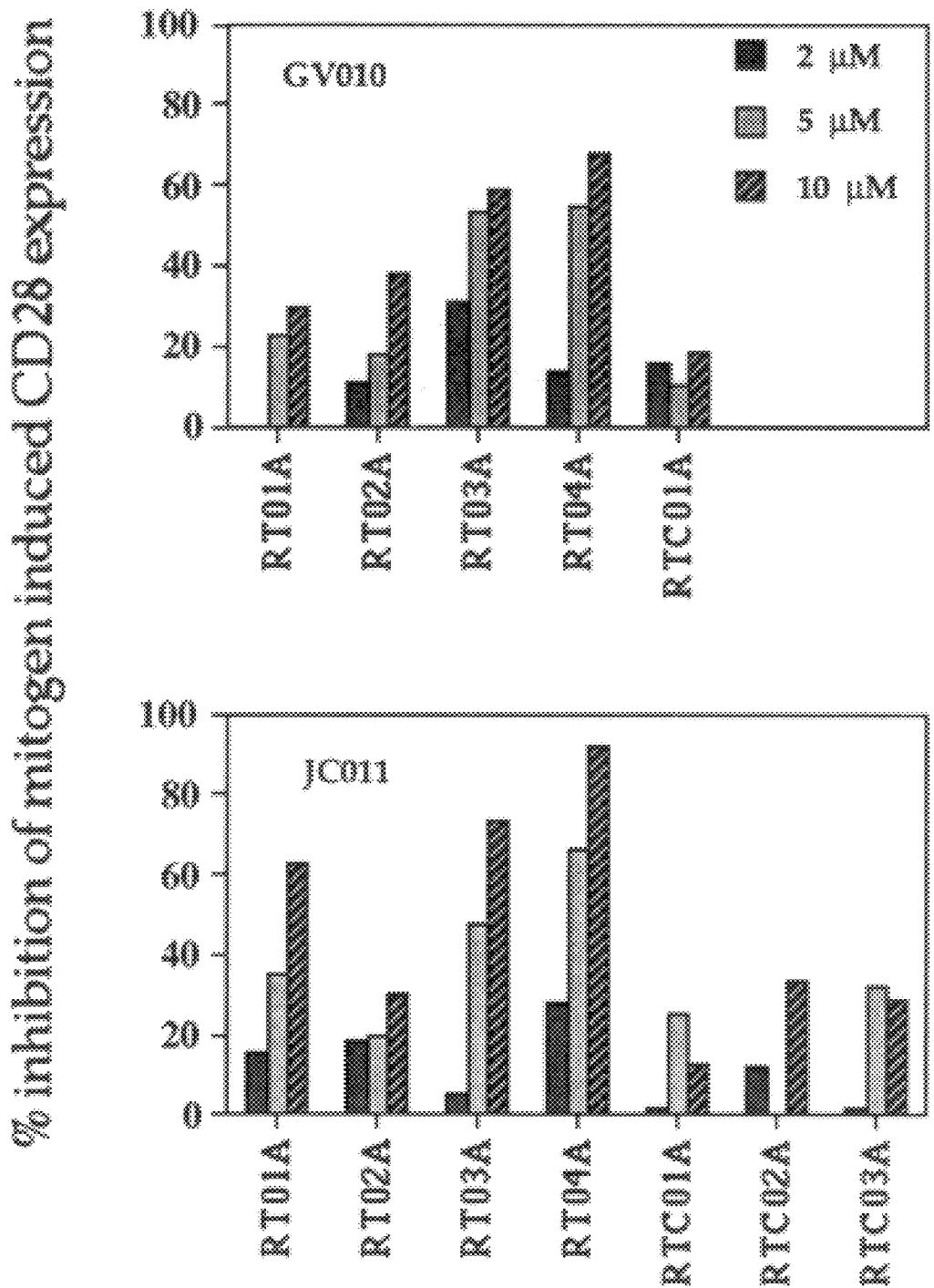

FIGS. 3A–C is a graphical representation of anti-CD3 monoclonal antibody/PMA-induced CD28 expression in human T-cells from two donors (GV010 and JC011), (A) and the effect of CD28-specific and control phosphorothioate (B, batch 1 and 2) and phosphorothioate-3'hydroxypropylamine (C) oligonucleotides on anti-CD3 monoclonal antibody/PMA-induced CD28 expression in peripheral blood T-cells from the same 2 donors.

FIGS. 4A & B is a graphical representation of A) the induction of T-cell proliferation by mitogens in human T-cells from donor KS006 and B) the effect of CD28-specific and control phosphorothioate oligonucleotides on anti-CD3 monoclonal antibody/PMA-induced human T-cell proliferation.

Figure 5A:
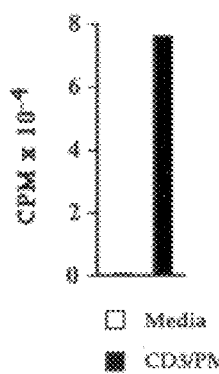
Figure 5B:
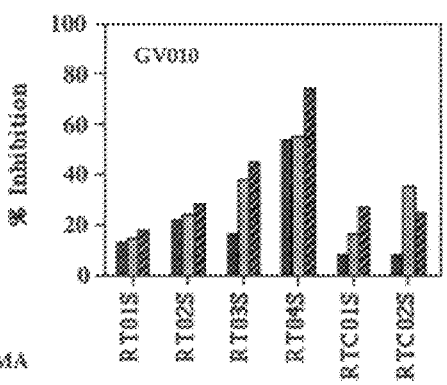
Figure 5C:
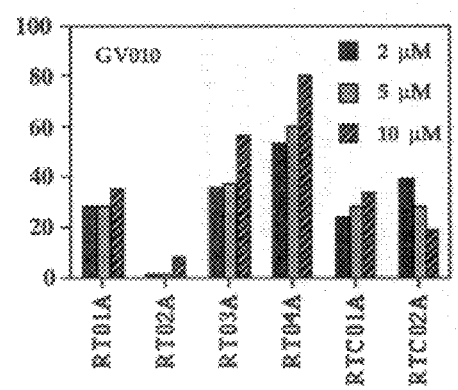

FIGS. 5A–C is a graphical representation of the induction of interleukin-2 (IL-2) production by anti-CD3 monoclonal antibody and PMA in human T-cells (A) and the effect of CD28-specific and control phosphorothioate (B) phosphorothioate-3'hydroxypropylamine (C) oligonucleotides on anti-CD3 monoclonal antibody/PMA-induced IL-2 production in human peripheral T-cells.

FIGS. 6A–C is a graphical representation of the induction of interferon-gamma (IFNγ) production by anti-CD3 monoclonal antibody and PMA in human T-cells (A) and the effect of CD28-specific and control phosphorothioate (B) phosphorothioate-3'hydroxypropylamine (C) oligonucleotides on anti-CD3 monoclonal antibody/PMA-induced interferon-gamma production in human peripheral T-cells.

Figure 7A:
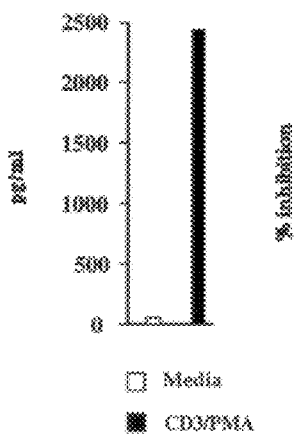
Figure 7B:
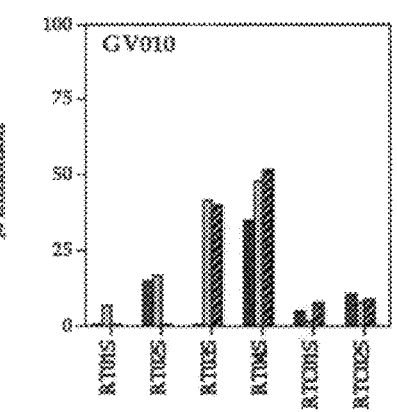
Figure 7C:
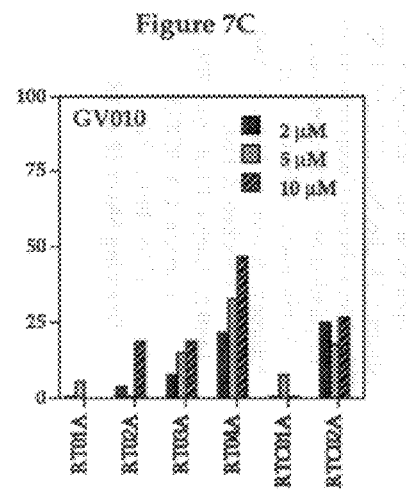

FIGS. 7A–C is a graphical representation of the induction of interleukin-8 (IL-8) production by anti-CD3 monoclonal antibody and PMA in human T-cells (A) and the effect of CD28-specific and control phosphorothioate (B) phosphorothioate-3'hydroxypropylamine (C) oligonucleotides on anti-CD3 monoclonal antibody/PMA-induced IL-8 production in human peripheral T-cells.

Figure 8A:
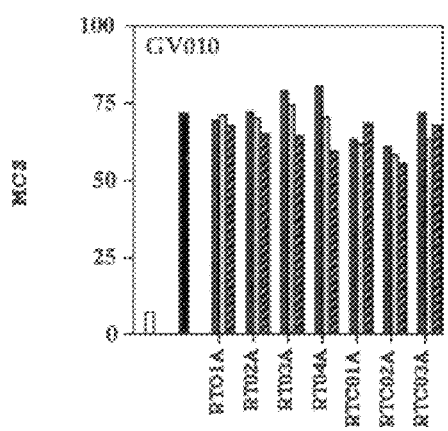

FIGS. 8A & B is a graphical representation of the induction of interleukin-2 receptor (IL-2R, otherwise known as CD25) (A) and intracellular adhesion molecule-1 (ICAM-1 otherwise known as CD54) (B) expression by anti-CD3 monoclonal antibody and PMA in human peripheral T-cells treated with and without CD28-specific and control phosphorothioate 3'hydroxypropylamine oligonucleotides.

FIGS. 9A–C is a graphical representation of CD28 expression in HUT 78 (A) and Jurkat (B) human T-cell lines before and after anti-CD3 monoclonal antibody and PMA treatment, and the effect of CD28-specific phosphorothioate oligonucleotides in anti-CD3 monoclonal antibody and PMA-treated Jurkat cells (C).

Figure 10:
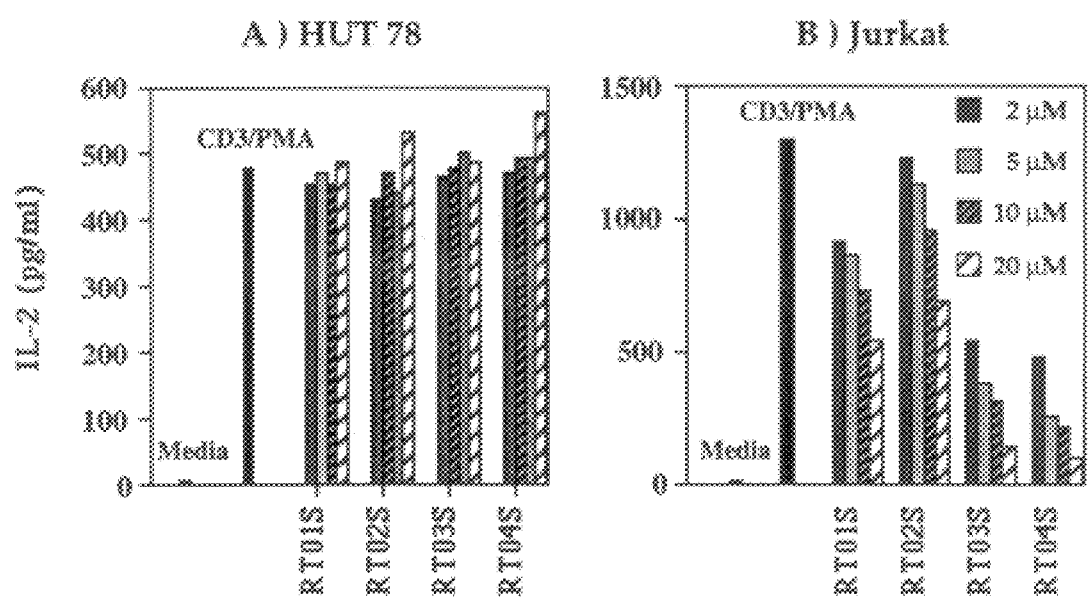

FIGS. 10A & B is a graphical representation of the effect of CD28-specific phosphorothioate oligonucleotides on interleukin-2 production in anti-CD3 monoclonal antibody and PMA-treated HUT 78 (A) and Jurkat (B) human T-cell lines.

FIGS. 11A–F is a graphical representation of the effect of phosphorothioate oligonucleotides on surface expression of accessory molecules and on cytokine secretion in activated T cells.

Figure 12:
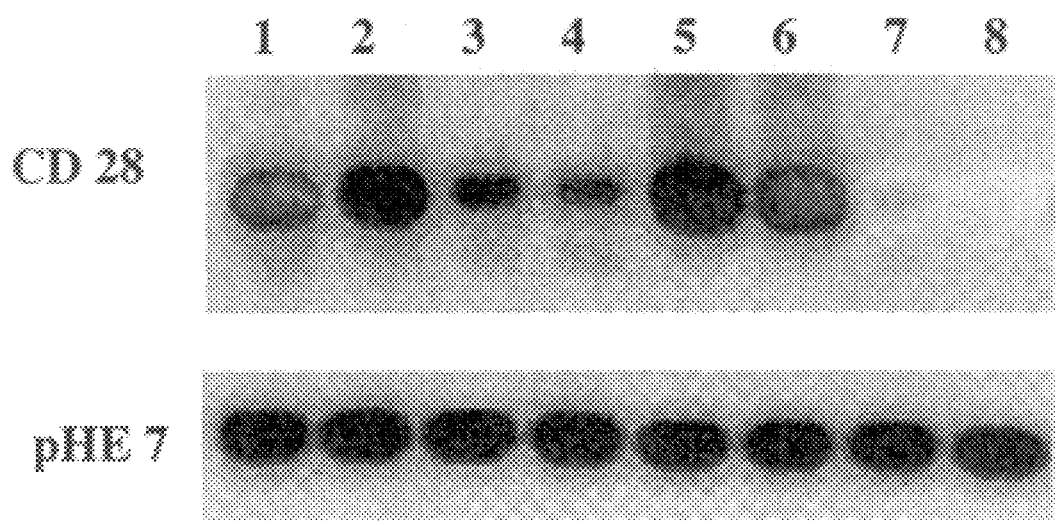
Figure 13:
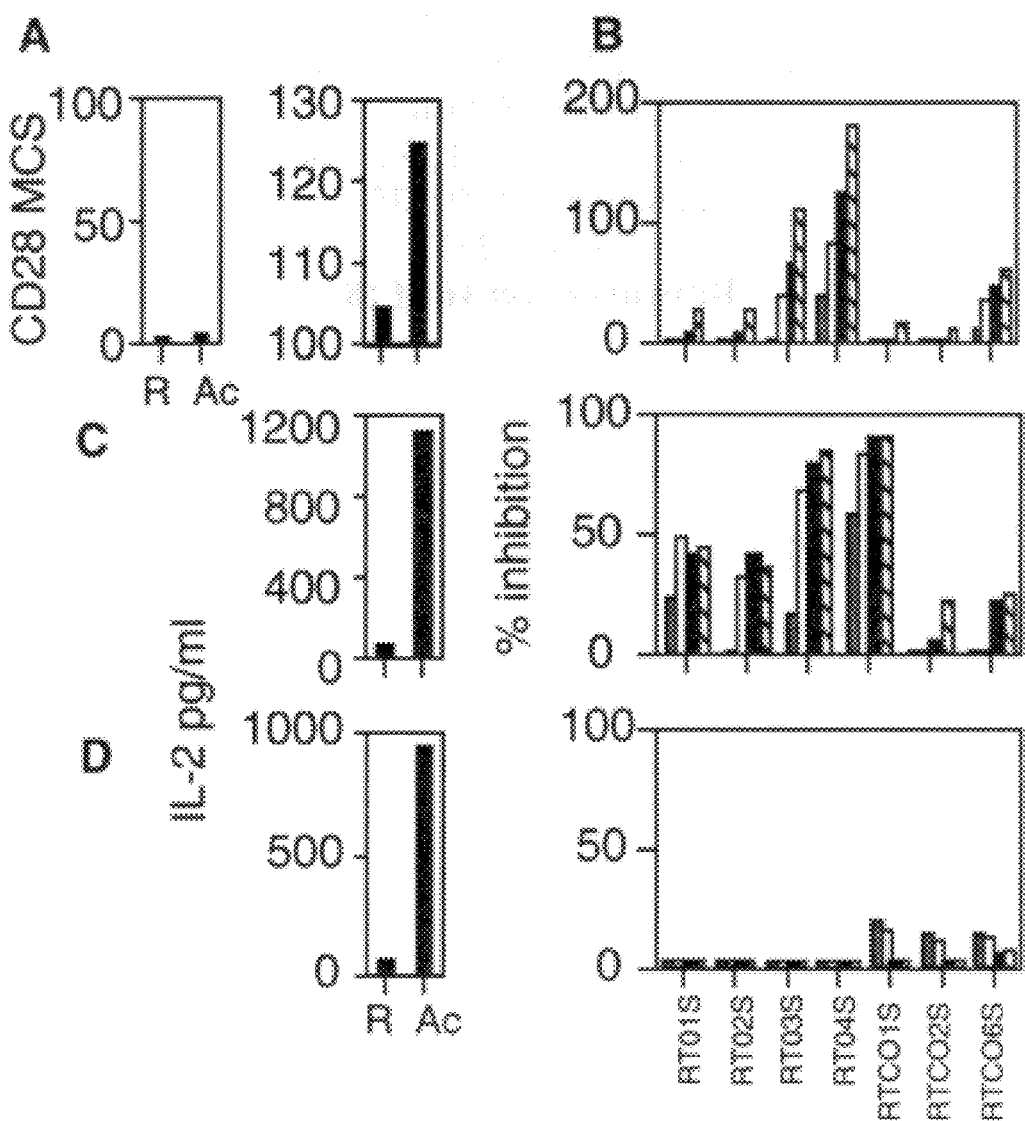

FIG. 12 is a graphical representation of the effect of phosphorothioate oligonucleotides on CD28 and CD25 mRNA levels.

FIGS. 13A–D is a graphical representation of the specificity of oligonucleotides RT03S (SEQ ID NO: 44) and RT04S (SEQ ID NO: 45) with respect to inhibitory effect on functional CD28 expression.

FIGS. 14A–H is a graphical representation of the tolerance induction in vitro by the CD28-specific oligonucleotides, RT03S (SEQ ID NO: 44) and RT04S (SEQ ID NO: 45).

FIGS. 15A & B is a graphical representation of the in vitro stability of $^{32}$P-labeled phosphorothioates, RT03S (SEQ ID NO: 44) and RTC06S (SEQ ID NO: 48) in extracellular supernatants (top panel) and Jurkat cell lysates (bottom panel).

V. DETAILED DESCRIPTION OF SPECIFIC EMBODIMENTS

Described herein are methods and compositions for treating immune system-mediated diseases, wherein the desired therapeutic effect is achieved by decreasing the expression of CD28, thereby abrogating activated CD28$^+$ T cell function and decreasing activation of other immune system cells. The inventor has discovered that antigen-dependent T cell activation may be inhibited by decreasing the expression of CD28 in CD28$^+$ T cells. The invention provides numerous compounds that may be used to decrease the expression of CD28 in T cells.

The invention described herein involves the discovery that decreasing CD28 expression in T cells can interfere with the antigen-specific activation of T cells. The discovery may be used to provide numerous methods of treating immune system-mediated diseases with oligomers targeted to CD28 and with non-oligomer compounds that decrease CD28 expression. By employing the discoveries of the biological effects of decreasing CD28 expression as described in this application, numerous methods of treating immune system-mediated diseases are provided, such methods may employ non-oligomer compounds that have not yet been synthesized or purified.

One aspect of the invention is to provide for oligomers that can be used to inhibit gene expression of certain genes is an established technique frequently referred to as the use of "anti-sense" oligonucleotides or "anti-sense therapy." Numerous publications on the construction and use of anti-sense are available. Exemplary of such publications are: Stein et al., *Science*, 261:1004–1012 (1993); Milligan, et al., *J. Med. Chem.*, 36:1923–1937 (1993); Helene, et al., *J. Biochim. Biophys. Acta*, 1049:99–125 (1990); Wagner, *Nature.*, 372:333–335 (1994); and Crooke and Lebleu, *Anti-sense Research and Applications*, CRC Press, Boca Raton (1993). The term "anti-sense" as used herein, unless indicated otherwise, refers to oligomers (including oligonucleotides) capable of forming either double-stranded or triple-stranded (triplex) helices with polynucleotides so as to interfere with gene expression. The principles of anti-sense design and use described in these publications, and other similar publications, may be used by the person of ordinary skill in the art to design, make, and use various embodiments of the CD28 specific oligomers of the invention.

The oligomers of the invention are capable of modulating the expression of the CD28 gene. The oligomers of the invention include those oligomers that have the property of being able to form either a double-stranded polynucleotide helix by hybridizing with CD28 transcripts (or portions thereof), or a double-stranded polynucleotide helix by hybridizing with a portion or portions of a CD28 gene, wherein the helix formation may occur under intracellular conditions. The oligomers of the invention also include those oligomers that are capable of affecting the regulation of gene expression such as by acting as molecular decoys and preventing protein-nucleic acid interaction of transcription factors with regulatory elements of the untranslated regions of the CD28 gene. Additionally, the oligomers of the invention include those oligomers that are capable of forming a triple-stranded polynucleotide helix with a portion or portions of a CD28 gene, wherein the helix formation may occur under intracellular conditions. Both double-stranded helix and triple-stranded helix base pairing relationships between nucleic acid bases (e.g., adenine-thymine, cytosine-guanine, uracil-thymine) are known to the person of ordinary skill in the art and may be employed in the design of the oligomers of the invention. Regions of the CD28 gene or CD28 gene transcript at which double-stranded helix or triple-stranded helix formation can occur with a given oligomer of the invention are said to be "targeted" by that oligomer.

Human CD28 is a 90-kDa homodimeric transmembrane glycoprotein present on the surface of a subset of T cells. CD28 is present on most CD4$^+$ T cells and about 50% of CD8$^+$ T cells. The DNA sequence encoding human CD28 has been resolved as can be found, among other places, in Lee et al. *Journal of Immunology*, 145:344–352 (1990) and on publicly accessible gene databases such as GenBank. The human CD28 gene comprises four exons, each defining a functional domain of the predicted protein. Transcription products of varying sizes have been observed to be produced from the human CD28 gene. The oligomers of the invention may be designed by referring to the published nucleotide sequence of the CD28 gene or the sequence of CD28 gene-derived cDNAs. The compositions and methods of the invention may be readily adapted for use in mammals other than humans by referring to the sequence of the CD28 gene from nonhuman mammals. the sequence of non-human CD28 gene may be obtained by, among other methods, using previously identified CD28 gene sequences from humans (or other mammals) as gene library hybridization probes and/or PCR (polymerase chain reaction) amplification primers. While the published nucleotide sequences of the CD28 gene are believed to be accurate, the subject invention may be practiced by the person of ordinary skill in the art even if the published nucleotide base sequence of CD28 contains sequencing errors. The proper nucleotide base sequence errors in published sequences may be detected by, among other means, re-sequencing regions of the CD28 gene (or CD28 gene transcripts) targeted by the oligomers of the invention. Resequencing may be performed by means of conventional DNA sequencing technology.

The oligomers of the invention preferably comprise from about 11 to about 50 nucleic acid base units. It will be readily appreciated by the person of ordinary skill in the art that oligomers of the invention may be significantly longer than 50 nucleic acid base units. In a more preferred embodiment of the invention, the oligomers comprise from about 8 to about 25 nucleic acid base units; more preferably from about 14 nucleic acid base units to about 22 nucleic base units. The preferred size limitations for the oligomers of the invention pertain only to those oligomers that are to be administered extracellularly to a cell and are not applicable to intracellularly produced CD28 specific oligomers, e.g., as produced from vectors for the genetic manipulation of target host cells.

The oligomers of the invention may have numerous different nucleic acid base sequences. The oligomers of the invention may be selected to reduce expression of CD28 by hybridizing (through nucleic acid—nucleic acid interaction) to virtually any region of a CD28 transcript of CD28 gene in order to reduce expression of CD28, or by hybridizing (through nucleic acid—protein interaction) to non-nucleic acid molecules that recognize untranslated sequences of the CD28 gene. For example, oligomers of the invention may be selected so as to be able to hybridize to translated regions of a CD28 transcript, untranslated regions of a CD28 transcript, unspliced regions of a CD28 transcript, CD28 gene introns, CD28 promoter sequences, and CD28 regulatory sequence, the 5' cap region of a CD28 transcript, CD28 gene coding regions, and the like (including combinations of various distinct regions). Preferred embodiments of the CD28 gene and CD28 gene transcripts by the oligomers of the invention are in the translational and/or transcriptional initiation regions of the CD28 gene (and transcripts thereof). By varying the location of the CD28 or CD28 gene transcript in which helix formation may occur through the selection of the nucleic acid base pair sequence of the oligomer, the potency of the oligomer, i.e., the amount required to produce the desired biological effect will be varied. Preferred embodiments of the oligomers of the invention have the highest possible potency. The potency of different oligomers of the invention may be measured by various in vitro assays known to the person of ordinary skill in the art. Examples of such assays can be found in the experiments section of this application. The person of ordinary skill in the art will appreciate that it not desirable to produce oligomers that are targeted to polynucleotide sequences that are also present at gene locations other than the CD28 gene. For example, it would be undesirable to produce an oligomer targeted to the Alu sequence in the 5' untranslated region of the CD28 transcript (the Alu region of the CD28 is described in Lee et al., *Journal of Immunology*, 145:344–352 (1990)). The use of oligomers that form double-stranded or triple-stranded helices with gene or transcripts of genes other than CD28 may be minimized by performing homology searches of oligomer nucleotide base sequences against polynucleotide sequence information present in publicly accessible data bases such as GenBank.

In a preferred embodiment of the invention, the subject oligomers exhibit perfect nucleic acid base complementarity to the selected target sequence, i.e., every nucleic acid base in the oligomer may enter into a base pairing relationship with a second (or third) nucleic acid base on another strand of a double (or triple) helix. However, a person of ordinary skill in the art will appreciate that various oligomers specific for a CD28 gene target and/or capable of inhibiting CD28 expression may have nucleotide base sequences that lack perfect hybridization to the CD28 gene (either strand), CD28 gene transcripts, or CD28-specific regulatory proteins.

In preferred embodiments of the oligomers of the invention are oligomers having the following nucleotide base sequences:

5'TTGTCCTGACGATGGGCTA3' (SEQ ID NO:1) RT01

5'AGCAGCCTGAGCATCTTTGT3' (SEQ ID NO:2) RT02

5'TTGGAGGGGGTGGTGGGG3' (SEQ ID NO:3) RT03

5'GGGTTGGAGGGGGTGGTGGGG3' (SEQ ID NO:4) RT04

In particularly preferred embodiments of the invention, the oligomers having the nucleotide base sequences indicated in RT01, RT02, RT03, and RT04, are phosphorothioates. Particularly preferred oligomers are phosphorothioate-3'hydroxypropylamine, as described in Tam et al., *Nucl. Acid. Res.* 22:977–986 (1994).

Oligomers of the invention may be designed so as to decrease the expression of CD28 in T cells that have internalized extracellularly applied oligomers of the invention. Additionally, oligomers of the invention may be designed so as to decrease expression of CD28 when the oligomers are produced intracellularly through the use of genetic expression vectors. Inhibition of CD28 expression may be effected through (I) interference with CD28 gene transcription, (ii) interference with the transcription of CD28 gene transcripts, (iii) interference with the processing of CD28 gene transcripts, or any combination of (I), (ii), and (iii). The precise degree and mechanism of the interference of CD28 expression will depend on factors such as the structure of the particular oligomer, the nucleotide base sequence of the oligomer, the dosage of oligomer, the means of administering the subject oligomer, and the like.

The term "oligomer" as used herein refers to both naturally occurring polynucleotides, e.g., DNA, RNA, and to various artificial analogs of naturally occurring nucleic acids that have the ability to form either double-stranded or triple-stranded helix with DNA or RNA. Many oligomers that are artificial analogs of naturally occurring polynucleotides have properties that make them superior to DNA or RNA for use in the methods of the invention. These properties include higher affinity for DNA/RNA, endonuclease resistance, exonuclease resistance, lipid solubility, RNAse H activation, and the like. For example, enhanced lipid solubility and/or resistance to nuclease digestion results by substituting an alkyl group or alkoxy group for a phosphate oxygen in the internucleotide phosphodiester linkage to form an alkylphosphonate oligonucleotide or alkylphosphotriester oligonucleotide. Non-ionic oligomers such as these are characterized by increased resistance to nuclease hydrolysis and/or increased cellular uptake, while retaining the ability to form stable complexes with complementary nucleic acid sequences.

While numerous oligomers that are analogs of naturally occurring nucleic acids are explicitly described herein, and/or are otherwise known to the person of ordinary skill in the art, it will be appreciated that numerous oligomers that are nucleic acid analogs that may be developed in the future may be readily adapted by those of ordinary skill in the art to inhibit the expression of CD28 genes. A brief review of different currently available DNA/RNA analogs that may be used as oligomers of the invention by selection of the appropriate nucleic acid base sequence so as to target CD28 genes (and transcripts thereof) is provided below. The various oligomers described in those publications are examples, not limitations, of different possible embodiments of oligomers that may be adapted for inhibition of CD28 expression in the methods and compositions of the invention.

Methylphosphonate (and other alkyl phosphonate) oligomers can be prepared by a variety of methods, both in solution and on insoluble polymer supports (Agrawal and Fiftina, *Nucl. Acids Res.*, 6:3009–3024 (1979); Miller et al., *Biochemistry*, 18:5134–5142 (1979); Miller et al., *J. Biol. Chem.*, 255:9659–9665 (1980); Miller et al., *Nucl. Acids Res.*, 11:5189–5204 (1983); Miller et al., *Nucl. Acids Res.*, 11:6225–6242 (1983); Miller et al., *Biochemistry*, 25:5092–5097 (1986); Sinha et al., *Tetrahedron Lett.* 24:877–880 (1983); Dorman et al., *Tetrahedron*, 40:95–102 (1984); Jager and Engels, *Tetrahedron Lett.*, 25:1437–1440 (1984); Noble et al., *Nucl. Acids Res.*, 12:3387–3404 (1984)

Callahan et al., *Proc. Natl. Acad. Sci. USA*, 83:1617–1621 (1986); Koziolkiewicz et al., *Chemica Scripta*, 26:251–260 (1986); Agrawal and Goodchild, *Tetrahedron Lett.*, 38:3539–3542 (1987); Lesnikowski et al., *Tetrahedron Lett.*, 28:5535–5538 (1987); Sarin et al., *Proc. Natl. Acad. Sci. USA*, 85:7448–7451 (1988).

Additional oligoribonucleotide analogs for use as oligomers are described in Inova et al., *Nucleic Acids Res.*, 15:6131 (1987) (2'-O-methylribonucleotides), Inova et al., *FEBS Lett.*, 215:327 (1987).

Descriptions of how to make and use phosphorothioates and phosphorodithioates can be found in, among other places, the following publications: U.S. Pat. No. 5,292,875, U.S. Pat. No. 5,286,717, U.S. Pat. No. 5,276,019, U.S. Pat. No. 5,264,423, U.S. Pat. No. 5,218,103, U.S. Pat. No. 5,194,428, U.S. Pat. No. 5,183,885, U.S. Pat. No. 5,166,387, U.S. Pat. No. 5,151,510, U.S. Pat. No. 5,120,846, U.S. Pat. No. 4,814,448, U.S. Pat. No. 4,814,451, U.S. Pat. No. 4,096,210, U.S. Pat. No. 4,094,873, U.S. Pat. No. 4,092,312, U.S. Pat. No. 4,016,225, U.S. Pat. No. 4,007,197, U.S. Pat. No. 3,972,887, U.S. Pat. No. 3,917,621, and U.S. Pat. No. 3,907,815, Dagle et al., *Nucl. Acids Res.* 18:4751–4757 (1990), Loke et al., *Proc. Natl. Acad. Sci. USA*, 86:3474–3478 (1989), LaPlanche, et al., *Nucleic Acids Res.*, 14:9081 (1986) and by Stec, et al., *J. Am. Chem. Soc.* 106:6077 (1984), and Stein et al., *Nucl. Acids Res.* 16:3209–3221 (1988).

Descriptions of how to make and use phosphoramidates can be found in among other places the following publications: Agrawal et al., *Proc. Natl. Acad. Sci.*, 85:7079–7083 (1988), Dagle et al., *Nucl. Acids Res.*, 18(6):4751–4757 (1990), Dagle et al., *Nucl. Acids Res.* 19(8):1805–1810 (1991), Other polynucleotide analogs of interest include compounds having acetals or thioacetals in the backbone structure. Examples of how to make and use such compounds can be found, among other places in, Gao et al., *Biochemistry* 31:6228–6236 (1992), Quaedflieg et al., *Tetrahedron Lett.* 33(21):3081–3084 (1992), Jones et al., *J. Org. Chem.* 58:2983–2991 (1993).

Other polynucleotide analogs of interest include compounds having silyl and siloxy bridges in the backbone structure. Examples of how to make and use such compounds can be found, among other places in Ogilvie and Cormier, *Tetrahedron Lett.*, 26(35):4159–4162 (1985), Cormier and Ogilvie, *Nucl. Acids Res.* 16(10):4583–4594 (1988), PCT publication WO 94/06811.

Other polynucleotide analogs of interest include compounds having silyl and acetamidate bridges in the backbone structure. Examples of how to make and use such compounds can be found, among other places in Gait et al., *J. Chem. Soc.*, Perkin Trans. 1:1684 (1974), Mungall and Kaiser, *J. Org. Chem.* 42(4):703–706 (1977), and Coull et al., and *Tetrahedron Lett.* 28(7):745–748 (1987).

Polynucleotide analogs having morpholino-based backbone linkages have also been described. Information on how to make and use such nucleotide analogs can be found in, among other places, U.S. Pat. Nos. 5,034,506, 5,235,033, 5,034,506, 5,185,444.

Polynucleotide analogs having various amine, peptide, and other achiral and/or neutral linkages have been described: Caulfield et al., *Bioorganic & Medicinal Chem. Lett.*, 3(12):2771–2776 (1993), Mesmaeker et al., *Bioorganic & Medicinal Chem. Lett.*, 4(3):395–398 (1994); *Angew. Chem. Int. Ed. Engl.*, 33(2):226–229 (1994), U.S. Pat. No. 5,166,315, and U.S. Pat. No. 5,142,047.

Polynucleotides having thioether and other sulfur linkages between subunits are described in, among other places Schneider and Brenner, *Tetrahedron Lett.*, 31(3):335–338 (1990), Huang et al., *J. Org. Chem.*, 56:3869–3882 (1991); Musicki and Widlanski, *Tetrahedron Lett.*, 32(10):1267–1270 (1991); Huang and Widlanski, *Tetrahedron Lett.*, 33(19):2657–2660 (1992); and Reynolds et al., *J. Org. Chem.* 57:2983–2985 (1992), and PCT publication WO 91/15500.

Other polynucleotide analogs of interest include peptide nucleic acids (PNAs) and related polynucleotide analogs. A description of how to make and use peptide nucleic acids can be found in, among other places, Buchardt et al., *Trends in Biotech.*, 11 (1993) and PCT publication WO 93/12129.

Other oligomers for use in anti-sense inhibition have been described in Thuong et al., *Proc. Natl. Acad. Sci.*, 84:5129–5133 (1987), U.S. Pat. No. 5,217,866, Lamond, *Biochem. Soc. Transactions*, 21:1–8 (1993) (2'-O-alkyloligoribonucleotides), Ono et al., *Bioconjugate Chemistry*, 4:499–508 (1993) (2'-deoxyuridine analogs carrying an amino linker at the 1'-position of deoxyribose), Kawasai et al., *J. Med. Chem.*, 36:831–841 (1993) (2'-deoxy-2'-fluoro phosphorothioate oligonucleotides), PCT publication WO 93/23570, Augustyns et al., *Nucl. Acids Res.*, 21(20):4670–4676 (1993).

Additionally, oligomers may be further modified so as to increase the stability of duplexes and/or increase cellular uptake. Examples of such modifications can be found in PCT publication WO 93/24507 entitled "Conformationally Restrained Oligomers Containing Amide or Carbamate Linkages for Sequence-Specific Binding," Nielsen et al., *Science*, 254:1497–1500 (1991), PCT publication WO 92/05186 entitled "Modified Internucleoside Linkages," PCT publication WO 91/06629, filed Oct. 24, 1990 and U.S. Pat. No. 5,264,562 filed Apr. 24, 1991, both of which are entitled "Oligonucleotide Analogs with Novel Linkages," PCT publication WO 91/13080 entitled "Pseudonucleosides and Psuedonucleotides and their Polymers," PCT publication WO 91/06556 entitled "2'-Modified Oligonucleotides," PCT publication WO 90/15065 filed on Jun. 5, 1990 entitled "Exonuclease Resistant Oligonucleotides and Methods for Preparing the Same," and U.S. Pat. No. 5,256,775.

The oligomers of the invention comprise various nucleic acid bases. In addition to nucleic acid bases found to occur naturally in DNA or RNA, e.g., cytosine, adenine, guanine, thymidine, uracil, and hypoxanthine, the oligomers of the invention may comprise one or more nucleic acid bases that are synthetic analogs of naturally occurring acid bases. Such non-naturally occurring heterocyclic bases include, but are not limited to, aza and deaza pyrimidine analogs, aza and deaza purine analogs as well as other heterocyclic base analogs, wherein one or more of the carbon and nitrogen atoms of the purine and pyrimidine rings have been substituted by heteroatoms, e.g., oxygen, sulfur, selenium, phosphorus, and the like. Preferred base moieties are those bases that may be incorporated into one strand of double-stranded polynucleotides so as to maintain a base pairing structural relationship with a naturally occurring base on the complementary strand at the double-stranded polynucleotide.

The invention provides many methods of treating a variety of immune disorders. The terms "treatment" or "treating" as used herein with reference to a disease refers both to prophylaxis and to the amelioration of symptoms already present in an individual. It will be appreciated by the person of ordinary skill in the art that a treatment need not be completely effective in preventing the onset of a disease or in reducing the symptoms associated with the disease. Any reduction of the severity of symptoms, delay in the onset of symptoms, or delay in the progression of severity of symptoms is desirable to a patient. Immune disorders that can be treated by the methods of the invention include the diseases in which CD28 expressing T cells mediate or contribute to an undesired idiopathic effect. Inhibition of CD28 expression results in the decrease of expression of cytokines normally produced by activated CD28$^+$ T cell, such cytokines include interleukin-2, interferon gamma, and interleukin-8. Accordingly, the methods of the invention include, but are not limited to, methods of treating diseases in which pathogenesis is mediated through interleukin-2, interferon-gamma, interleukin-8, or a combination thereof, whereby a T cell mediated immune response is interrupted or reduced. Examples of immune disorders that may be treated by administering the subject oligomers to a patient include organ transplantation rejection, septic shock, tumor-induced cachexia, and numerous auto-immune diseases. Autoimmune diseases that may be treated by the subject methods include diseases that are mediated by aberrant T cell activation including Type I (insulin-dependent) diabetes, thyroiditis, sarcoidosis, multiple sclerosis, autoimmune uveitis, ulcerative colitis, aplastic anemia, systemic lupus erythematosus, rheumatoid arthritis, parasite induced inflammation and granulomas, Crohn's disease, psoriasis, polymyositis, dermatomyositis, scleroderma, vasculitides, psoriatic arthritis, Graves disease, myasthenia gravis, autoimmune hepatobilliary disease, and the like. Additionally, the methods and compositions of the invention provide for the treatment of a variety of syndromes, including septic shock and tumor-induced cachexia, in which the pathogenic effects are mediated, at least in part, by the lymphokine secreted from activated CD28$^+$ T cells.

The disease treatment methods of the invention comprise the steps of administering an effective amount of the subject oligomers to a patient. The precise dosage, i.e., effective amount, of CD28-specific oligomer to be administered to a patient will vary with numerous factors such as the specific disease to be treated, the precise oligomer (or oligomers) in the therapeutic composition, the age and condition of the patient, and the like. Protocols for determining suitable pharmaceutical dosages are well known to those of ordinary skill in the art and can be found, among other places, in Remington's *Pharmaceutical Science* (latest edition), Mack Publishing Company, Easton, Pa., and the like.

In addition to administering the CD28 targeted oligomers directly to a patient, the invention contemplates methods of treatment in which CD28$^+$ cells (or cells having the potential to express CD28) are removed from a patient (with or without other cells) and transformed with one or more different oligomers of the invention. Transformation may be by any of a variety of means well known to the person skilled in the art, e.g., electroporation, cationic lipids such as DOTMA or DOSPA, and the like. Transformed cells may then be reintroduced into the body.

Another aspect of the invention is to provide methods of treating immune disorder by means of administering CD28-specific oligomers, wherein the oligomers are produced intracellularly through recombinant polynucleotide expression vectors. Intracellularly-produced CD28-specific oligomers are necessarily RNA or DNA molecules. Recombinant polynucleotide vectors for the expression of polynucleotide sequences of interest are well known to the person of ordinary skill in the art of molecular biology. Detailed descriptions of recombinant vectors for the expression of polynucleotides of interest can be found in, among other places, "Somatic Gene Therapy," ed. P. L. Chang, CRC Press, Boca Raton (1995), R. C. Mulligan, *Science,* 260:926–932 (1993), F. W. Anderson, *Science,* 256:808–873 (1992), Culver et al., *Hum. Gene Ther.,* 2:107–109 (1991), and the like. Suitable recombinant vectors for use in the subject methods of treating immune disorders through genetic engineering are either able to integrate into the genome of T cells or replicate in the cytoplasm of T cells. CD28-specific oligomers for use in intracellular administration are preferably significantly longer than CD28-specific oligomers for extracellular administration. In a preferred embodiment of the subject methods of intracellular CD28 administration, the CD28-specific oligomer is complementary to one or more entire CD28 transcripts or the entire CD28 gene; however, suitable intracellularly-produced CD28-specific oligomers may be considerably shorter in length. Unlike extra-cellularly-administered CD28-specific oligomers, CD28-specific oligomers do not present problems with intracellular uptake or hydrolysis by extracellular enzymes. The subject methods of using intracellular CD28-specific oligomers may involve administering CD28-specific oligomer-encoding recombinant vectors directly to a patient. Alternatively, CD28-specific oligomer-producing vectors may be administered directly to cells that have been removed from a patient (i.e., stem cells, T cells, whole blood, marrow, etc.), whereby transformed cells are produced. The transformed cells may be subsequently be reintroduced into a patient.

The invention also specifically provides for expression vectors capable of expressing one or more of the oligomers of the invention. Generally, such expression vectors comprise, in operable combination, a promoter and a polynucleotide sequence encoding an oligomer capable of inhibiting the expression of CD28 in a T cell. Although many different promoters may be used in the vectors of the invention, preferred promoters are capable of driving the high level expression in T cells. The expression vectors of the invention may also comprise various regulatory sequences. Currently available expression vectors, especially those vectors explicitly designed for gene therapy, may readily be adapted for the expression of CD28-targeted oligomers of the invention. The vectors may be adapted for the expression of CD28-targeted oligomers using conventional genetic engineering techniques such as those described in Sambrook et al., *Molecular Cloning,* 2nd Ed., Cold Spring Harbor Press, Cold Spring Harbor, N.Y. (1989).

Another aspect of the invention is to provide pharmaceutical formulations for the administration of the oligomers of the invention so as to effect the treatment of immune system-mediated diseases. These pharmaceutical formulations may be readily produced by the person of ordinary skill in the art of pharmaceutical science. Such formulations comprise one or more of the oligomers of the invention; however, in embodiments of the invention comprising more than one different types of oligomers, the oligomers are preferably selected so as to not be able to hybridize with one another. The pharmaceutical formulations of the invention may be adapted for administration to the body in a number of ways suitable for the selected method of administration, including orally, intravenously, intramuscularly, intraperitoneally, topically, and the like. In addition to comprising one or more different oligomers of the invention, the subject pharmaceutical formulations may comprise one or more nonbiologically active compounds, i.e., excipients, such as stabilizers (to promote long term storage), emulsifiers, binding agents, thickening agents, salts, preservatives, and the like.

Formulations for parenteral administration may include sterile aqueous solutions, which may also contain buffers, diluents, and other suitable additives. Pharmaceutical formulations of the invention may be designed to promote the cellular uptake of the oligomers in the composition, e.g., the oligomers may be encapsulated in suitable liposomes.

Pharmaceutical formulations for topical administration are especially useful for localized treatment. Formulations for topical treatment included ointments, sprays, gels, suspensions, lotions, creams, and the like. Formulations for topical administration may include, in addition to the subject oligomers, known carrier materials such as isopropanol, glycerol, paraffin, stearyl alcohol, polyethylene glycol, etc. The pharmaceutically acceptable carrier may also include a known chemical absorption promoter. Examples of absorption promoters are e.g., dimethylacetamide (U.S. Pat. No. 3,472,931), trichloro-ethanol or trifluoroethanol (U.S. Pat. No. 3,891,757), certain alcohols and mixtures thereof (British Patent No. 1,001,949), and British patent specification No. 1,464,975.

In addition to the therapeutic uses of the subject oligomers, the oligomers may also be used as an analytical laboratory tool for the study of T cell activation. T cells have several surface receptors in addition to CD28 and the antigen specific T cell receptors. Difficulties arise in studying the individual biological properties of selected receptors because of potential and actual interactions between multiple receptor-mediated pathways. By providing a mechanism for decreasing CD28 expression in T cells, the oligomers and methods of the invention also provide useful laboratory methods for studying T cell behavior independently of the CD28 activation pathway.

The invention may be better understood by referring to the following examples. The following examples are offered for the purpose of illustrating the invention and should not be interpreted as a limitation of the invention.

VI. EXAMPLES—SERIES 1

Oligonucleotides

Oligodeoxynucleotides were synthesized on an automated DNA synthesizer (Applied Biosystems model 394) using standard phosphoramidite chemistry. β-cyanoethylphosphoramidites, synthesis reagents and CPG polystyrene columns were purchased from Applied Biosystems (ABI, Foster City, Calif.). 3'-AminoModifier C3 CPG columns were purchased from Glen Research (Sterling, Va.). For phosphorothioate oligonucleotides, the standard oxidation bottle was replaced with tetraethylthiuram disulfide/acetonitrile, and the standard ABI phosphorothioate program was used for the stepwise addition of phosphorothioate linkages. After cleavage from the controlled pore glass column, the protecting groups were removed by treating the oligonucleotides with concentrated ammonium hydroxide at 55° C. for 8 hours. The oligonucleotides were purified by HPLC using a reverse phase semiprep C8 column (ABI). Following cleavage of the DMT protecting group, treatment with 80% acetic acid and ethanol precipitation, the purity of the product was assessed by HPLC using an analytical C18 column (Beckman, Fullerton, Calif.). All oligonucleotides of >90% purity were lyophilized to dryness. Oligonucleotides were reconstituted in sterile deionized water (ICN, Costa Mesa), adjusted to 400 μM following evaluation of OD260 nm, aliquoted and stored at −20° C. prior to experimentation. In all cases, at least three batches of each oligonucleotide listed in Table 1 were used.

Cell lines and T cell purification

Peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×10$^6$ T-cells were then incubated overnight at 37° C. in 20–30 ml RPMI-AP5 (RPMI-1640 medium (ICN, Costa Mesa, Calif.) containing 20 μM HEPES buffer, pH 7.4, 5% autologous plasma, 1% L-glutamine, 1% penicillin/streptomycin and 0.05% 2-mercaptoethanol) to remove any contaminating adherent cells. In all experiments, T-cells were washed with RPMI-AP5 and then plated on 96-well microtitre plates at a cell concentration of 2–3×10$^6$ cells/ml.

TABLE 1

| OLIGO ID | SEQUENCE | SEQ ID NO: | TYPE | TARGET | RESIDUE NO. |
| --- | --- | --- | --- | --- | --- |
| RT01 | TTG TCC TGA CGA TGG GCT A | 1 | AS | 5' untranslated region | 89–107 |
| RT02 | AGC AGC CTG AGC ATC TTT GT | 2 | AS | AUG codon | 94–113 |
| RT03 | TTG GAG GGG GTG GTG GGG | 3 | TF | 5' untranslated region | 58–75 |
| RT04 | GGG TTG GAG GGG GTG GTG GGG | 4 | TF | 5' untranslated region | 58–78 |
| RTC01 | TAG CCC ATC GTC AGG ACA A | 5 | SS | sense strand control for RT01 | |
| RTC02 | ACA AAG ATG CTC AGG CTG CT | 6 | SS | sense strand control for RT02 | |
| RTC03 | CTC CAG CCA ATC GGA AGG CTC TTT AA | 7 | RO | random oligo | |
| RTC04 | TTT TGG TTG GTG TGG TTT GTG | 8 | GT | GT control for RT03, RT04 | |
| RTC05 | GTG TGT GTG TGT GTG TGT GTG | 9 | GT | GT control for RT03, RT04 | |
| RTC06 | AAC CTC CCC CAC CAC CCC | 10 | SS | sense strand control for RT03, RT04 | |

AS: Antisense
SS: Sense
TF: Triplex forming
RO: Random oligo

TABLE 2

| OLIGO ID | SEQUENCE | SEQ ID NO: | TYPE | TARGET | RESIDUE NO. |
| --- | --- | --- | --- | --- | --- |
| RT05 | AGT TGA GAG CCA AGA GCA GC | 11 | AS | AUG codon | 108–127 |
| RT06 | GCT AAG GTT GAC CGC ATT GT | 12 | AS | AUG codon | 197–216 |
| RT07 | AGT CCT TTG TGA AGG GAT GC | 13 | AS | coding region | 256–275 |

TABLE 2-continued

| OLIGO ID | SEQUENCE | SEQ ID NO: | TYPE | TARGET | RESIDUE NO. |
| --- | --- | --- | --- | --- | --- |
| RT08 | ACC TGA AGC TGC TGG GAG TA | 14 | AS | coding region | 313–332 |
| RT09 | CCC AAT TTC CCA TCA CAG TT | 15 | AS | coding region | 352–371 |
| RT10 | GCA AGC TAT AGC AAG CCA GG | 16 | AS | coding region | 585–604 |
| RT11 | CAG GAG CCT GCT CCT CTT AC | 17 | AS | coding region | 641–660 |
| RT12 | GTG TCA GGA GCG ATA GGC TG | 18 | AS | coding region | 746–765 |
| RT13 | GGC CTG TCA CAG GAA ATC TC | 19 | AS | coding region | 949–968 |
| RT14 | AGC CGG CTG GCT TCT G | 20 | AS | stop codon | 777–792 |
| RT15 | AAA TTG GCA TTG GTG GGC C | 21 | AS | 3' untranslated region | 873–890 |
| RT16 | TAA GTT GGA ATG TGG GCC AT | 22 | AS | 3' untranslated region | 984–1003 |
| RT17 | CTC CCA GAA TCC ACT CCC TT | 23 | AS | 3' untranslated region | 1049–1068 |
| RT18 | GCT TGA CTG AGA TGT GCA GG | 24 | AS | 3' untranslated region | 1089–1108 |
| RT19 | TCC TAG CCT TTC TTC TGC AA | 25 | AS | 3' untranslated region | 1136–1155 |
| RT20 | CGT ACG CTA CAA GCA TGG G | 26 | AS | coding region | 178–196 |
| RT21 | TGA GAA AGG GAA GAG GCT CC | 27 | AS | 3' untranslated region | 1065–1088 |
| RT22 | GAA GTC GCG TGG TGG G | 28 | AS | coding region | 729–744 |
| RT23 | AAA TTA GCC AGG CAT CAT GG | 29 | AS | 5' untranslated region | −325 to −306 |
| RT24 | AGT GGG TGG ATC ATT TGA GG | 30 | AS | 5' untranslated region | −244 to −225 |
| RT25 | TGC TTG AAA TCC AGC AGA GA | 31 | AS | 5' untranslated region | −139 to −120 |
| RT26 | CAT GAT GGG CTT ATG GGA AT | 32 | AS | 5' AP-1 like element | −60 to −79 |
| RT27 | CAG TGG CTC ACG CCT GTA | 33 | AS | 5' untranslated region | −201 to −184 |
| RT28 | GGG GTT GGT TGG TTG TTT GG | 34 | TF | 5' AP-1 like element | −518 to −499 |
| RT29 | GTG TTT GTG TGG GGT TT | 35 | TF | 5' AP-1 like element | −158 to −142 |
| RT30 | GGG GTT TTT TGT GTG GT | 36 | TF | 5' AP-1 like element | −148 to −132 |

AS: Antisense
TF: Triplex forming

The T-cell lymphoma cell lines, Jurkat E6-1 (CD28+/CD4+) cells (152-TIB) and HUT 78 (CD28−/CD4+) cells (TIB-161) (ATCC, Rockville, Md.) were maintained in RPMI-10 (RPMI-1640 medium containing 20 $\mu$M HEPES buffer, pH 7.4, 10% fetal calf serum (FCS) (Hyclone, Logan, Utah), 1% L-glutamine and 1% penicillin/streptomycin).

Mitogen-induced T-cell activation and oligonucleotide treatment

Prior to the addition of human peripheral T-cells or T-cell lymphoma cell lines (0.2–0.3×10$^6$), duplicate 96-well microtitre plates were pre-coated with purified anti-CD3 monoclonal antibody (mAb) (6.25–200 ng/well) (clone HIT 3a, Pharmingen, San Diego, Calif.) and washed twice with cold phosphate-buffered saline, pH 7.4 (PBS). Anti-CD3 mAb-treated T-cells were further activated by the addition of 2 ng phorbol 12-myristate 13-acetate (PMA) (Calbiochem, La Jolla, Calif.) and incubated for 48 h at 37° C. Anti-CD3/PMA-activated T-cells were treated with 1–20 $\mu$M CD28-specific and control oligonucleotides immediately following activation and re-treated 24 h later. T-cells from one duplicate plate was used for immunofluorescence analysis and the supernatants used for cytokine studies and the second plate was used for T-cell proliferation analysis.

Immunofluorescence studies

Following activation, 150 ml cell supernatant from the first duplicate microplate was transferred to another microplate for analysis of cell-derived cytokine production. The remaining cells were washed twice with isotonic saline solution, pH 7.4 (Becton Dickinson, Mansfield, Mass.) and resuspended in 50 ml isotonic saline solution and split into two samples. One sample aliquot was co-stained with either PE-CD28/FITC-CD4 or PE-CD54/FITC-CD25 mAb and non-specific fluorescence was assessed by staining the second aliquot with PE/FITC-labeled isotype-matched control monoclonal antibody. All fluorescence-labeled monoclonal antibodies were obtained from Becton Dickinson (San Jose, Calif.). Incubations were performed in the dark at 4° C. for 45 min using saturating mAb concentrations. Unincorporated label was removed by washing in PBS prior to the analysis with a FACScan flow cytometer (Becton Dickinson). Antigen density was indirectly determined in gated live cells and expressed as the mean channel of fluorescence (MCF). Surface expression of specific antigens (CD54, CD25) was represented as the mean channel shift (MCS) obtained by subtracting the MCF of FITC- or PE-labeled isotype-matched (IgG1) control mAb-stained cells from the MCF of FITC- or PE-labeled antigen-specific mAb stained cells. Alternatively, surface expression of the CD4$^+$-subset of cells stained with CD28 mAb was determined by subtracting the MCF of CD28$^+$ CD4$^+$ from the MCF of CD28$^+$ CD4$^−$ cells. The viability of control untreated and oligonucleotide-treated cells were determined in each batch of all oligonucleotides in multiple donors by staining with the vital dye, propidium iodide (5 $\mu$g/ml final concentration). The percentage of live cells which excluded propidium iodide was determined by flow cytometry and was >90% (range 90–99%) following treatment with all batches of all oligonucleotides at a dose range of 1–20 $\mu$M (FIG. 2).

Cytokine analyses

Cell-derived human cytokine concentrations were determined in cell supernatants from the first duplicate microplate. Mitogen-induced changes in interleukin-2 (IL-2) levels were determined using a commercially available ELISA kit (R & D systems Quantikine kit, Minneapolis, Minn.) or by bioassay using the IL-2-dependent cell line, CTLL-2 (ATCC, Rockville, Md.). Mitogen-induced changes in interferon-gamma and interleukin-8 (IL-8) levels were determined by ELISA using kits from Endogen (Cambridge, Mass.) and R & D systems (Quantikine kit, Minneapolis, Minn.) respectively. All ELISA results were expressed as pg/ml and the CTLL-2 bioassay as counts per minute representing the IL-2 -dependent cellular incorporation of $^3$H-thymidine (ICN, Costa Mesa, Calif.) by CTLL-2 cells.

T-cell proliferation assay

The second duplicate microplate in all experiments were analyzed for changes in mitogen-induced T-cell proliferation. 72 h following anti-CD3/PMA activation and in the absence or presence of oligonucleotides, cells were pulsed with 1 $\mu$Ci $^3$H-thymidine (ICN, Costa Mesa, Calif.) and incubated overnight at 37° C. Mitogen-induced cell growth, as assessed by incorporation of radioactive label, was determined by harvesting the cells and scintillation counting on a Wallac Betaplate counter (Wallac, Gaithersburg, Md.).

Inhibition of CD28 expression in activated human T-cells by CD28-specific oligonucleotides Anti-CD3/PMA treatment of human T-cells increased the surface expression of CD28 (using immunofluorescence analysis) from a MCS of 122±7.74 in resting T-cells to a MCS of 150±9.27 (n=9). The difference in CD28 expression in resting and activated T-cells is defined as mitogen-induced CD28 expression (FIG. 3A). FIGS. 3B and 3C shows the treatment of anti-CD3/PMA-activated T-cells with phosphorothioate (denoted as S-oligomers, FIG. 3B) and phosphorothioate-3' amine (denoted as A-oligomers, FIG. 3C) forms of CD28-specific and control oligonucleotides in 2 donors and with 2 separate batches of each oligonucleotide. Of the four candidate oligonucleotides, RT01–RT04, (Table 1), in the dose range 2–10 $\mu$M, both phosphorothioate and phosphorothioate-3' amine forms of RT03 and RT04 were the most active inhibitors of mitogen-induced CD28 expression, both inhibiting induced CD28 expression by greater than 50% ($IC_{50}$) at 5 $\mu$M or less. These two oligonucleotides, which differ in length, were designed to hybridize with a stretch of double-stranded DNA, 5' upstream of the transcription initiation site of the CD28 gene. No similar dose-dependent inhibition of mitogen-induced CD28 expression was observed with the control oligonucleotides, RTC01 (SEQ ID NO: 5)–RTC06 (SEQ ID NO: 10) (Table 1). All experiments were performed on at least three batches of each oligonucleotide using T-cells from 7 donors. The fact that oligonucleotide regulation of CD28 expression was demonstrable in human T-cells is critical because peripheral, epidermal and dermal T-lymphocytes are the intended target of CD28-specific oligonucleotides.

Inhibition of mitogen-induced T-cell proliferation by CD28-specific oligonucleotides The mitogenic effect of anti-CD3/PMA treatment was demonstrable by the augmented proliferation observed following the activation of resting T-cells. The incorporation of $^3$H-thymidine, represented as counts per minute, was 301641±47856 (n=9) in activated T-cells and 650±566 (n=9) in resting T-cells. The effect of anti-CD3 and PMA on T-cell proliferation are synergistic as shown in FIG. 4A. FIG. 4B shows a representative experiment of the effect of CD28-specific and control phosphorothioate oligonucleotides on anti-CD3/PMA-activated T-cell proliferation. In at least seven separate experiments, all in the dose range 2–10 $\mu$M, both phosphorothioate (data not shown) and phosphorothioate-3' amine (FIG. 4B) forms of RT03 and RT04 were the most active inhibitors of mitogen-induced T-cell proliferation, inhibiting T-cell proliferation by up to 45%. No similar dose-dependent inhibition of mitogen-induced T-cell proliferation was observed with the control oligonucleotides, RTC01 (SEQ ID NO: 6)–RTC06 (SEQ ID NO: 10). Here, treatment with CD28-specific oligonucleotides, RT03 and RT04, could reverse the hyper-proliferation of activated T-cells thus demonstrating that regulation of the CD28 pathway had a significant effect on one vital biological function of T-cell activation, T-cell proliferation.

Inhibition of activated T-cell-derived cytokine production by CD28-specific oligonucleotides Activated T-cells produce a variety of immunomodulatory cytokines including IL-2, interferon-gamma and IL-8. CD28-inducible restriction elements for IL-2 and IL-8 have been demonstrated in the promoter sequences for both genes and have subsequently been shown to be regulated by the CD28 pathway (Fraser et al., (1991) Science 251:313–316, Seder et al., (1994) J. Exp. Med. 179:299–304). Interferon-gamma also has been shown to be regulated by the CD28 pathway (Wechsler et al., J. Immunol., 153:2515–2523 (1994)). Anti-CD3/PMA treatment of resting T-cells dramatically increased the T-cell -derived levels of all three cytokines (FIGS. 5A, 6A and 7A). FIGS. 5, 6 and 7 respectively depict the effect of phosphorothioate (B) and phosphorothioate-3' amine © versions of CD28-specific and control oligonucleotides on IL-2, interferon-gamma, and IL-8 production in activated T-cells from the same representative donor. The CD28-specific oligonucleotides, RT03 (SEQ ID NO: 3) and RT04 (SEQ ID NO: 4) but not the control oligonucleotides, RTC01 (SEQ ID NO: 5)–RTC06 (SEQ ID NO: 10) (data not shown)), inhibited mitogen-induced IL-2, interferon-gamma, and IL-8 production in activated T-cells in a dose-dependent manner. Both phosphorothioate ($IC_{50}$ 5 $\mu$M) and phosphorothioate-3' amine ($IC_{50}$ 10 $\mu$M) forms of the CD28-specific oligonucleotides were equally active in the dose range 2–10 $\mu$M. Similar results for all three cytokines were seen with 4 or more different donors. These observations demonstrate that CD28-specific oligonucleotides were also capable of regulating multiple effector molecules of the CD28 pathway of T-cell activation.

Specificity of oligonucleotide inhibition of CD28 expression

The specificity of the CD28-specific oligonucleotides, RT03 and RT04 was evaluated by three methods.

(1) CD28-independent T-cell activation markers.

Figure 8B:
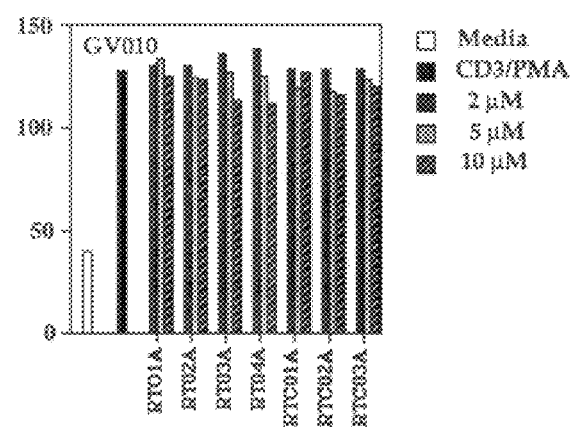

The first method was to determine whether these CD28-specific oligonucleotides were able to inhibit the expression of other human T-cell activation markers which act independently of the CD28 costimulatory pathway. Activation of resting T-cells significantly increases the expression of both the IL-2receptor (CD25) and the intracellular adhesion molecule, ICAM-1 (CD54). However, both these accessory molecules are regulated independently of the CD28 pathway (June et al., Mol. Cell Biol., 7:4472–4481 (1987), Damle et al., J. Immunol., 149:2541 (1992)). FIG. 8 shows the effect of CD28-specific and control oligonucleotides on CD25 (FIG. 8A) and CD54 (FIG. 8B) expression in mitogen-activated T-cells. No significant decrease in the activated T-cell expression of both CD25 and CD54 were observed following treatment with all CD28-specific and control oligonucleotides in the dose range 2–10 $\mu$M. This clearly demonstrates the specificity of the CD28-specific oligonucleotides in inhibiting expression of their target protein.

(2) CD28-negative T-cell line, HUT 78

The second method was to demonstrate that the CD28 pathway was really the target for CD28-specific oligonucleotides by comparing mitogen-induced IL-2 production in a CD28+, T-cell leukemia cell line, Jurkat E6-1 and a CD28-, T-cell lymphoma cell line, HUT 78. FIG. 9A confirms the absence of CD28 expression in both resting and activated HUT 78 cells whereas constitutive levels of CD28 increases upon activation in Jurkat E6-1 cells (FIG. 9B). In CD28+ Jurkat E6-1 cells, CD28-specific but not control oligonucleotides were able to inhibit mitogen-induced CD28 expression (FIG. 9C) and also mitogen-induced IL-2 production (FIG. 10B). In contrast, in CD28-HUT 78 cells, mitogen-induced IL-2 production was not affected by CD28-specific and control oligonucleotides (FIG. 10A). This clearly demonstrates the specificity of these oligonucleotides to inhibit only CD28-regulated IL-2 production.

(3) Specific activation of CD28 pathway

The third method was to activate resting T-cells specifically via the CD28 pathway using anti-CD28 monoclonal antibody in combination with mitogens (anti-CD3/PMA) using identical protocols to those used in activating T-cells with mitogens alone. Anti-CD28 mAb in combination with PMA or anti-CD3 mAb has been previously shown to provide the costimulatory signal to resting T-cells and promote only CD28-dependent and not TCR-dependent augmentation of T-cell proliferation and cytokine production (June et al., (1987) *Mol. Cell Biol.*, 7:4472–4481). Phosphorothioate and phosphorothioate-3' amine versions of CD28-specific but not control oligonucleotides were able to inhibit CD28-dependent activation of IL-2, IL-8 and interferon-gamma production and T-cell proliferation in anti-CD28/mitogen-activated resting T-cells (data not shown). This clearly demonstrates that only the CD28-specific oligonucleotides act only on the CD28 pathway of T-cell activation.

VII. EXAMPLES—SERIES 2

Oligonucleotides

Oligonucleotides were synthesized with an Applied Biosystems 394 DNA synthesizer. Phosphorothioate linkages were introduced after the standard oxidation bottle was replaced with tetraethyl-thiuram disulfide/acetonitrile. The purity of the oligonucleotides was assessed by analytical HPLC. All oligonucleotides of >90% purity were lyophilized to dryness and reconstituted in water (400 $\mu$M). At least three batches of each oligomer listed in Tables 3 and 5 were used. 5' labeling of oligonucleotides was achieved using T4 polynucleotide kinase and $^{32}$P-$\gamma$ATP.

T cell activation studies

Peripheral blood mononuclear cells (PBMCs) were isolated from healthy donors by density gradient centrifugation followed by T cell enrichment using Lymphokwik (One Lambda). Contaminating monocytes were removed by adherence to plastic. Purified T cells were >99% CD2$^+$, <1% HLA-DR$^+$ and <5% CD25$^+$. Jurkat E6-1 (CD28$^+$/CD4$^+$) T cells and HUT 78 (CD28$^-$/CD4$^+$) T cells and the monocytic cell line, THP were obtained from ATCC. Cells were cultured at a concentration of 0.2–0.3×10$^6$/well and activated with plate-immobilized anti-CD3 monoclonal antibody (mAb) (HIT3A 0.25 $\mu$g/ml) (Pharmingen) and 2 ng phorbol 12-myristate 13-acetate (PMA) (Calbiochem).

Immunofluorescence studies

Cells were co-stained with either PE-CD28/FITC-CD4 or PE-CD54/FITC-CD25 mAb or with PE/FITC-labeled isotype-matched controls (Becton Dickinson). Cell surface antigen density (CD28, CD54, CD25) was confirmed by flow cytometry (FACScan, Becton Dickinson). Viability was assessed by propidium iodide (5 $\mu$g/ml) exclusion in control untreated and oligo-treated CD4$^+$ cells from multiple donors and was typically >90% (range 90–99%) following 48 h incubation with 1–10 $\mu$M of each batch of all oligonucleotides.

Proliferation and cytokine assays

Proliferative responses were assessed by measuring $^3$H-thymidine (1 $\mu$Ci, ICN) incorporation for the last 16 h of each assay. Cells were harvested onto filters and DNA synthesis was measured following scintillation counting on a Wallac Betaplate counter. Cytokine concentrations in culture supernatants were assayed using ELISA kits for IL-2, IL-8 (R & D Systems) and IFN-$\gamma$ (Endogen) or by bioassay using the IL-2-dependent cell line, CTLL-2 (ATCC).

RT-PCR and Southern Analysis

Total cellular RNA was extracted using Trizol reagent (GIBCO/BRL). The cDNA synthesis reaction (Promega) was performed using oligomer (dT)$_{15}$ primer and AMV reverse transcriptase (H. C.). The PCR reaction (GeneAmp PCR kit, Perkin-Elmer Cetus) consisted of 50 $\mu$l mixture containing 3 $\mu$l of cDNA, dNTPs (each at 200 $\mu$M), 0.5 $\mu$M of each primer and 1 unit of Taq polymerase. The primers used were as follows:CD28, 5'-CTGCTCTTGGCTCTCAA CTT-3' (sense) and 5' AAGCTATAGCAA GCCAGGAC-3' (antisense), interleukin-2 receptor p55 alpha chain primers (Stratagene) and pHE7 ribosomal gene. Kao, H.-T., Nevins, J. R. (1983) *Mol. Cell. Biol.* 3, 2058–2065 Amplification conditions were 45 sec at 94° C., 1 min at 57° C. and 2 min at 72° C. for 35 cycles, followed by 8 min at 72° C. PCR products were separated on 2% agarose, transferred to Hybond N+ membrane (Amersham) in 20×SSC overnight and immobilized using 0.4M NaOH. Blots were hybridized with $^{32}$P-$\gamma$ATP labeled oligonucleotide probes. Washed blots were then analyzed using PhosphorImager.

MLR and alloantigen-specific T cell assays

For MLR responses, PBMCs were cultured (1:1) with mitomycin C-treated (50 $\mu$g/ml) PBMCs from a HLA-disparate individual. In alloantigen-specific T cell assays, T cells isolated from PBMCs of tetanus-toxoid-primed healthy donors were cultured (1:1) with autologous mitomycin C-treated PBMCs in the presence of tetanus toxoid (2 $\mu$g/ml, List Biologicals). In both assays, 2×10$^5$ cells/well were cultured for 6 days at 37° C. prior to further analysis.

In vitro oligonucleotide stability studies

Temporal oligonucleotide stability analyses were performed as described previously (Tam, R. C., Li, Y., Noonberg, S., Hwang, D. G., Lui, G., Hunt, C. A., Garovoy, M. R. (1994) *Nucleic Acids Res.* 22, 977–986). Oligonucleotide degradation profiles were assessed by electrophoresis and quantitated using Nickspin columns.

Figure 11:
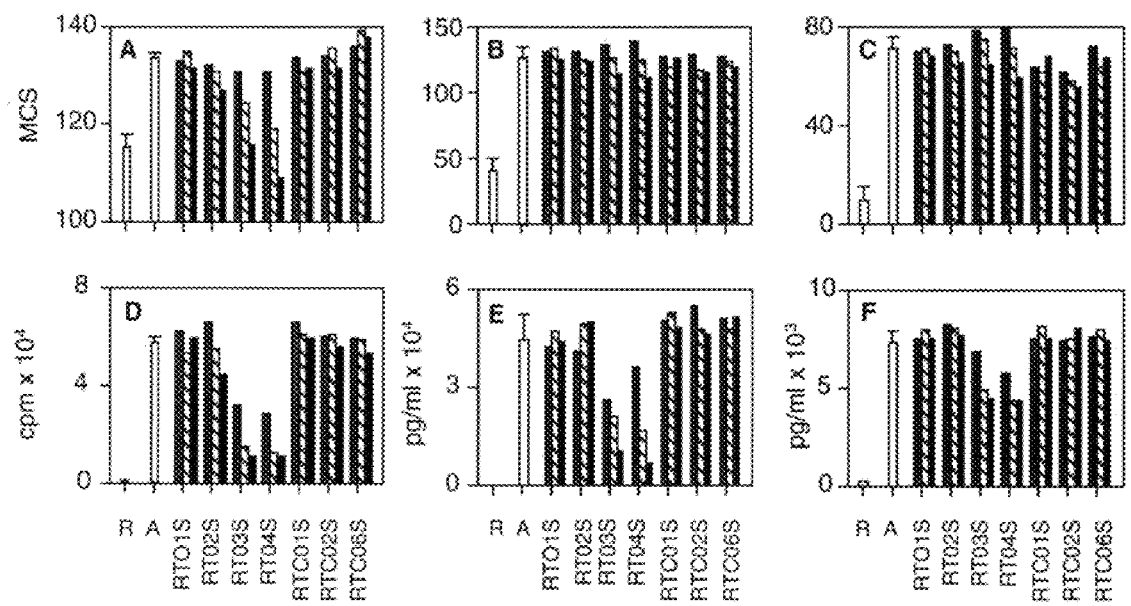

Inhibition of CD28 expression by phosphorothioate oligonucleotides is specific and affects activated T cell function FIG. 11 summarizes the effect of the phosphorothioate oligonucleotides from Table 3 on surface expression of accessory molecules and on cytokine secretion in activated T cells. The oligomers used were designed to hybridize to the 5' untranslated region (UT) of the CD28 gene, and were either antisense (AS) or G-rich sequences. Control oligomers were either sense strand (SS) or complementary strand (CS) sequences. 48 h treatment of resting T cells (R) with anti-CD3 antibody and PMA augmented the expression (Ac) of the accessory molecules, CD28(A), CD25(B) and CD54© and of the cytokines, IL-2 (D), IFN$\gamma$(E) and IL-8(F) Data are presented as mean standard deviation of triplicate samples. The cumulative effect of two additions (0 and 24 h) of 2 $\mu$M (■), 5 $\mu$M (◨) and 10 $\mu$M (▦) of the phosphorothioates from Table 3 on activation-induced T cell function was monitored by immunofluorescence analysis (accessory molecules) and by determination of secreted cytokine levels using CTLL-2 bioassay (IL-2) and ELISA (IFN$\gamma$, IL-8). Surface antigen density (MCS), in gated live CD4$^+$ cells was measured as the increase in mean channel of fluorescence compared to IgG1 controls. IL-2-dependent cellular incorporation of $^3$H-thymidine was measured as counts per minute (cpm) and immunoreactive IFN$\gamma$ and IL-8 as pg/ml. The data shown, all derived from experiments performed on T cells isolated from a single donor, are representative of experiments from 9 separate donors.

TABLE 3

Phosphorothioate oligonucleotides

| Oligo | Sequence (5' to 3') | Description | SEQ ID NO |
|---|---|---|---|
| RT01S | TTG TGG TGA CGA TGG GCT A | AS 5' UT 79-97 | 42 |
| RT02S | AGC AGC CTG AGC ATC TTT GT | AS 5' UT 94-113 | 43 |
| RT03S | TTG GAG GGG GTG GTG GGG | G-rich 5' UT 58-75 | 44 |
| RT04S | GGG TTG GAG GGG GTG GTG GGG | G-rich 5' UT 58-78 | 45 |
| RTC01S | TAG CCC ATC GTC AGG ACA A | SS to RT01 | 46 |
| RTC02S | ACA AAG ATG CTC AGG CTG CT | SS to RT02 | 47 |
| RTC06S | AAC CTC CCC CAC CAC CCC | CS to RT03 | 48 |

The data demonstrates that selected phosphorothioate oligomers (Table 3) can specifically block activation-induced CD28 expression in CD4+ T cells. In a representative donor (FIG. 11A), activation-induced CD28 expression but not IL-2receptor (CD25) or intracellular adhesion molecule-1 (ICAM-1 or CD54) expression, was inhibited in a dose-dependent manner by the phosphorothioate oligomers, RT03S (SEQ ID NO: 44) and RT04S (SEQ ID NO: 45) (IC$_{50}$≦5 μM). No similar inhibition was observed with the antisense oligomers, RT01S (SEQ ID NO: 42) or RT02S (SEQ ID NO: 43) or the control oligomers, RTC01S (SEQ ID NO: 46), RTC02S (SEQ ID NO: 47) and RTC06S (SEQ ID NO: 48). Furthermore, we provided evidence that the active oligomers modulated activation-induced CD28 by blocking transcription in activated human T cells. At 10 μM, RT03S (SEQ ID NO: 44) and RT04S (SEQ ID NO: 45) but not a representative control oligo, RTC06S (SEQ ID NO: 48), reduced expression of activation-induced levels of CD28 but not IL-2receptor mRNA (FIG. 12).

FIG. 12 shows the effect of phosphorothioate oligonucleotides at 10 μM on CD28 and CD25 mRNA levels. Resting (lane 1) and anti-CD3/PMA-activated (6 h) levels of CD28 and CD25 mRNA, in the absence (lane 2) or presence of the oligonucleotides, RT03S (SEQ ID NO: 44) (lane 4), RTC06S (SEQ ID NO: 64) (lane 5) and RT03D (SEQ ID NO: 49) (lane 6) were detected following RT-PCR of total cellular RNA and Southern analysis using specific, radiolabeled probes. The CD28 probe was derived from exon 2 (5'-ACGGGGTTC AACTGTGATGGGAAATTGGGCAA-3') and for IL-2receptor, the probe was generated from the original primer mix. Equivalent loading was assessed following hybridization with a probe generated from pHE7 sense primer. RNA from CD28-deficient HUT (7) and THP (8) cell lines were used as controls. The data shown are representative of 3 separate experiments.

Thus the specific inhibition of CD28 mRNA levels by biologically active phosphorothioates paralleled their effect on CD28 surface protein. Moreover, active oligomers abrogated activation-induced T cell function, as RT03S (SEQ ID NO: 44) and RT04S (SEQ ID NO: 45) but not RT01S (SEQ ID NO: 42) or RT02S (SEQ ID NO: 43) or the control oligomers, RTC01S (SEQ ID NO: 46), RTC02S (SEQ ID NO: 47) and RTC06S (SEQ ID NO: 48), markedly inhibited anti-CD3/PMA-induced synthesis of the cytokines, IL-2, IFNγ and IL-8 by activated T cells (IC$_{50}$≦5 μM, range 2–10 μM) (FIG. 11B).

As alternate costimulatory pathways can also induce lymphokine synthesis in activated T cells (Damle, N. K., Klussman, K., Linsley, P. S., Aruffo, A. (1992) *J. Immunol.* 148, 1985–1992), it was important to determine whether the biological activity of RT03S (SEQ ID NO: 44) and RT04S (SEQ ID NO: 45) was specific to functional CD28 expression. Accordingly, we compared the effect of phosphorothioates on anti-CD3/PMA-induced IL-2 production in a CD28+, T cell leukemia cell line, Jurkat E6-1 and a CD28−, T cell lymphoma cell line, HUT 78. As summarized in FIG. 13, 48 h treatment of resting cells (R) with anti-CD3 antibody and PMA increased CD28 expression (Ac) in Jurkat (A, right) but not HUT 78 (A, left) cells. However, activation augmented IL-2 production in Jurkat, (C left), and HUT 78 (D, left) cells. The active oligonucleotides, RT03S (SEQ ID NO: 44) and RT04S (SEQ ID NO: 45), at 1 μM (□) 2(M (■), 5 μM (◨) and 10 μM (▨) inhibited CD28 expression (B) and IL-2levels (C, right) in activated Jurkat cells but had no effect on CD28-independent IL-2secretion in activated HUT 78 cells (D, right). The data shown are representative of three separate experiments.

In FIG. 13A, immunocytofluorometric analysis confirmed the absence of CD28 expression in both resting and activated HUT 78 cells, whereas constitutive levels of CD28 increased upon activation in Jurkat E6-1 cells. Furthermore, in Jurkat E6-1 cells, RT03S (SEQ ID NO: 44) and RT04S (SEQ ID NO: 45) (range 1–10 μM) significantly inhibited both activation-induced CD28 expression (FIG. 13B) and IL-2 production (FIG. 13C). In contrast, although activated HUT 78 cells produced similar levels of IL-2, no comparable oligo-dependent inhibition of this lymphokine was observed (FIG. 13D).

We also demonstrated that T cell activation (expression of CD28, IL-2, IL-8 and IFNγ) directed by a specific anti-CD28 mAb in combination with anti-CD3, was blocked by biologically active phosphorothioate oligomers (data not shown). Direct crosslinking of CD28 molecules has been previously shown to promote only CD28-dependent and not TCR-dependent augmentation of T cell proliferation and cytokine production (June, C. H., Ledbetter, J. A., Gillespie, M. M., Lindsten, T., Thompson, C. B. (1987) *Mol. Cell Biol.* 7, 4472–4481.). Taken together, our data strongly suggests that bioactivity of the active oligomers was specific to the CD28 pathway of T cell activation.

Figure 14:
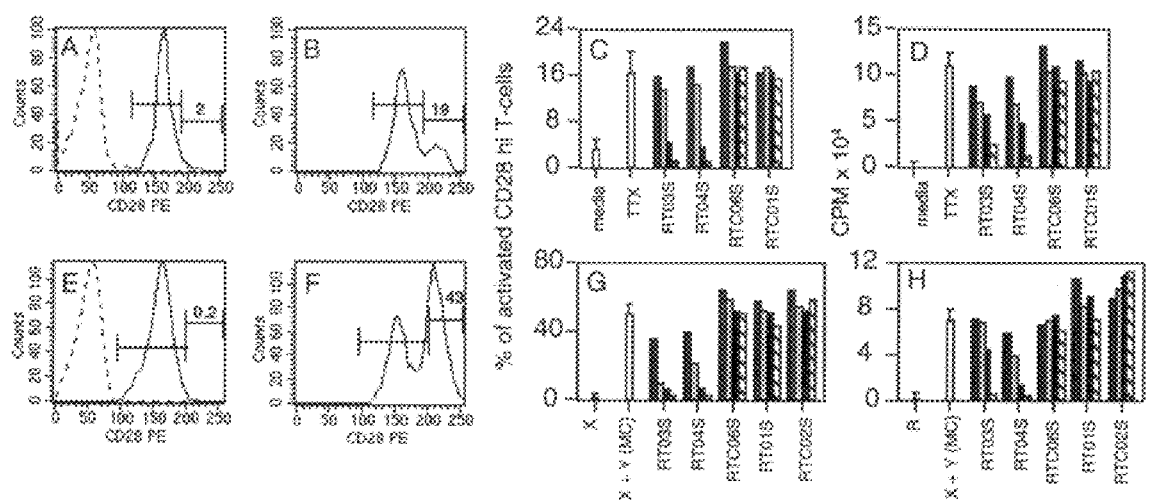

Inhibition of T cell proliferative responses in alloantigen-dependent T cell assay and primary allogeneic mixed lymphocyte reaction by phosphorothioate oligonucleotides We next compared the efficacy of the CD28-specific oligonucleotides, RT03S (SEQ ID NO: 44) and RT04S (SEQ ID NO: 45) in blocking antigen-specific primary immune responses in vitro. In FIG. 14, resting (A, B) and activated (E, F) levels of CD28 are indicated for tetanus toxoid-specific T cell assay (top panel, A and B) and mixed lymphocyte reaction (bottom panel, E and F). The percentage of CD4+, CD28-hi T cells is shown in the right-hand marker for A, B, E and F. Oligomer activity was assessed by the potential of two additions (0 and 96 h) of 1 μM (□) 2 μM (■), 5 μM (◨) and 10 μM (▨) phosphorothioate oligonucleotides from Table 1 to reduce the percentage of CD28-hi expressing T cells (C, G) and activated T cell proliferation (D, H) in each assay. Activation of T cells was induced in response to tetanus toxoid (top panel) or following stimulation of responder T cells (X) by mitomycin-C treated stimulator PBMCs (Y) (bottom panel). These data are representative of three separate experiments.

In FIG. 14, using both tetanus toxoid-specific T cell assay (FIG. 14B) and primary mixed lymphocyte reaction (FIG. 14F), we observed the appearance of a subpopulation of activation-induced CD28-hi expressing T cells after the 6 day assay period. Addition of RT03S (SEQ ID NO: 44) and RT04S (SEQ ID NO: 45) (2–10 μM) resulted in a dose-related diminution of CD28-hi expression (FIGS. 14C, 14G) and a corresponding decrease in tetanus toxoid-specific (FIG. 14D) and responder cell antigen-specific (FIG. 14H) T cell proliferation. No similar effect was observed with RT01S (SEQ ID NO: 42) or the control oligomers, RTC01S (SEQ ID NO: 46), RTC02S (SEQ ID NO: 47) or RTC06S (SEQ ID NO: 48).

In vitro oligonucleotide stability extends the biological activity of phosphorothioate oligonucleotides It is known that modification of oligomers with phosphorothioate internucleotide linkages can impart nuclease resistance and thus extend the in vitro bioactivity from 1–2 h to 24 h (Stein, C. A., Cheng, Y. C. (1993) *Science* 261, 1004–1012.). Table 4 shows the temporal effect of phosphorothioates, RT03S (SEQ ID NO: 44) and RTC06S (SEQ ID NO: 48) on surface CD28 expression in the continued presence © or following removal of oligonucleotide from the extracellular milieu on day 2 (D). Monitoring was performed by immunofluorocytometry. Results are expressed as the difference in surface antigen expression of activated T cells ($MCF_A$) and oligonucleotide-treated activated T cells ($MCF_X$). CD28 expression in resting T cells on day 2 to 4 was in the range 119–121. "ND" represents no distinguishable difference.

TABLE 4

Temporal activity of phosphorothioates following continuous or discontinuous oligonucleotide treatment

| | | | Differential CD28 expression ($MCF_A$ – $MCF_X$) | | | | |
|---|---|---|---|---|---|---|---|
| | | | RT03S (SEQ ID NO: 44) | | | RTC06S (SEQ ID NO: 47) | |
| Day | | $MCF_A$ | 0 | 5 | 10 | 0 | 5 | 10 |
| 2 | | 144.8 | 18.4 | 8.9 | 9.3 | 1.9 | 1.7 | ND |
| 3 | C | 135.6 | 21.9 | 15.9 | 5.1 | ND | ND | 3.2 |
| 3 | D | 136.8 | 18.3 | 11.8 | 7.1 | 1.7 | 3.8 | 1 |
| 4 | C | 128.9 | 18.2 | 9.7 | 6.1 | ND | ND | ND |
| 4 | D | 130.1 | 2.3 | ND | ND | ND | ND | ND |

As shown in Table 4, the duration of effect of RT03S (SEQ ID NO: 44) exceeded 24 h and persisted through day 2, 3 and 4, relative to oligomer dose. However, upon removal of RT03S (SEQ ID NO: 44), from the extracellular milieu on day 2, the inhibitory activity remained for 24 h and was then completely abolished within the next 24 h. No oligomer activity was observed with a representative control oligo, RTC06S (SEQ ID NO: 48) throughout the same time course. A similar phenomenon was observed with oligo-mediated inhibition of activated T cell proliferation (data not shown). Increased bioavailability provided by phosphorothioate modification alone cannot account for the remarkably prolonged bioactivity of RT03S (SEQ ID NO: 44). Therefore, we demonstrated that the extended duration of effect was associated with additional in vitro stability provided by the secondary structure of RT03S (SEQ ID NO: 44).

Figure 15:
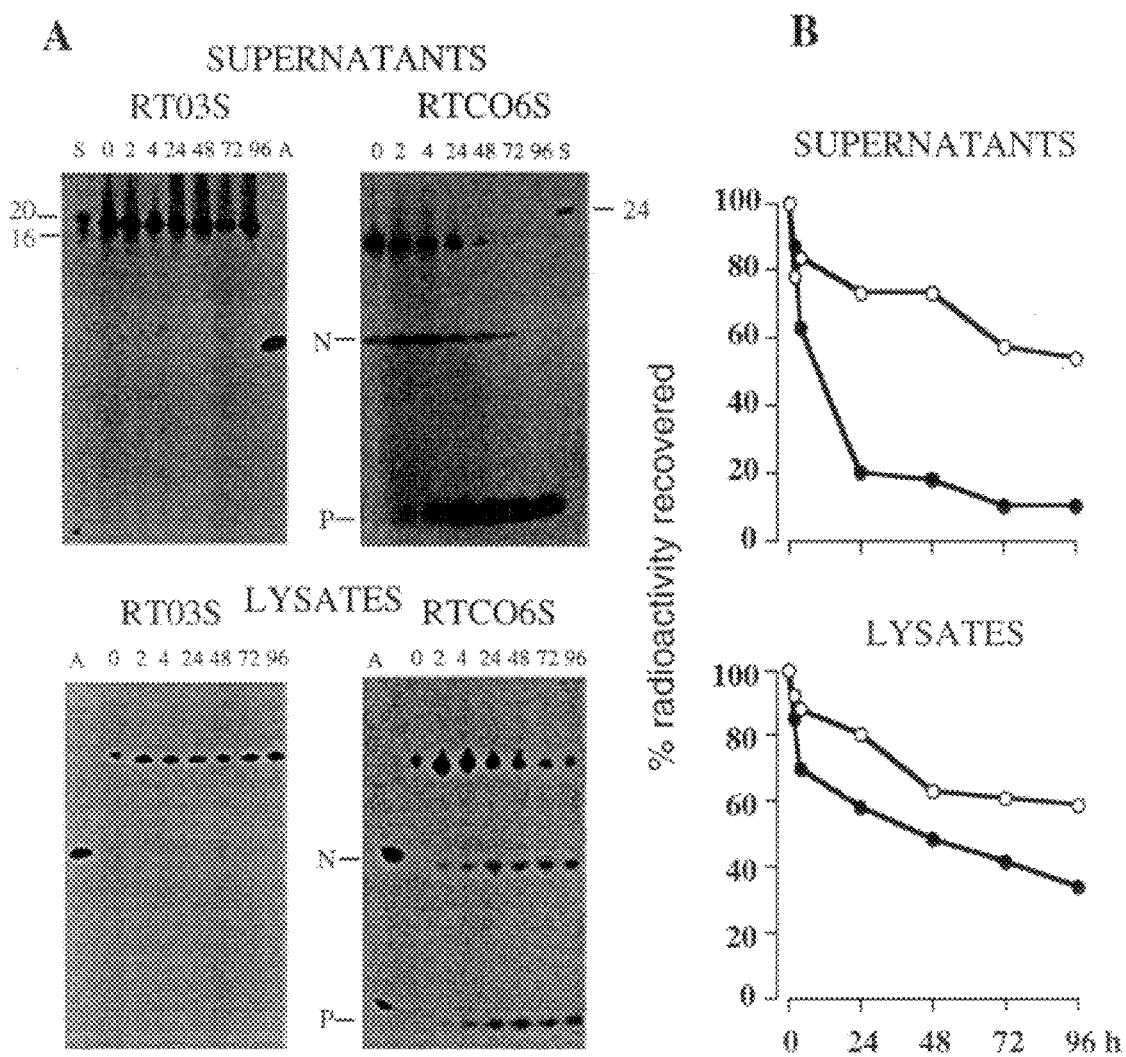

FIG. 15 summarizes test results on the in vitro stability of $^{32}$P-labeled phosphorothioates, RT03S (SEQ ID NO: 44) and RTC06S (SEQ ID NO: 48) in extracellular supernatants (top panel) and Jurkat cell lysates (bottom panel). (A) Time-dependent degradation (0–96 h) of each oligonucleotide (2000 cpm) was assessed by electrophoresis on a 20% polyacrylamide denaturing gel followed by visualization using a PhosphorImager. (B) The percentage of intact full length $^{32}$P-RT03S (SEQ ID NO: 44) (○) and $^{32}$P-RTC06S (SEQ ID NO: 48) (●) remaining at each time point, relative to t=0, was determined in eluates from 10000 cpm of extracellular supernatants and cell lysates applied through Nickspin columns (Pharmacia). Molecular weight standards (Std), $^{32}$P-dNTP (N) and free $^{32}$P-orthophosphate (P) were simultaneously analyzed.

In FIG. 15A, the electropherograms clearly show that, for both extracellular supernatants (S) and cell lysates (L), considerably more intact $^{32}$P-labeled RT03S (SEQ ID NO: 44) than RTC06S (SEQ ID NO: 48) remained following a 96 h incubation with Jurkat cells. Consistent with this observation are the Nickspin column data (FIG. 15B). Here, the percentage of intact oligomer recovered from RT03S (SEQ ID NO: 44) after 96 h was 54% (S) and 59% (L) and from RTC06S (SEQ ID NO: 48) was 10% (S) and 34% (L). In addition, secondary structure alone is not sufficient to account for the increased nuclease resistance and duration of bioactivity of RT03S (SEQ ID NO: 44) as its phosphodiester counterpart, RT03D had little bioactivity (Table 5) and from in vitro stability studies, only had a half-life of 24 h (data not shown). Table 5. Identification of oligonucleotide sequence responsible for inhibition of CD28 expression and CD28-dependent IL-2 production

| | | * Relative inhibition of expression | | |
|---|---|---|---|---|
| Oligo | Sequence | CD28 | IL-2 | SEQ ID NO: |
| RT03S (D) | TTG GAG GGG G TG GTG GGG | 100 (3) | 100 (44) | 44 (49) |
| RT11S | GGG GAG GAG GGG CTG GAA | 100 | 100 | 50 |
| RT04S | GGG TTG GAG GGG GTG GTG GGG | 123 | 100 | 45 |
| RT05S | TTG GAG GGG GAG GAG GGG | 136 | 100 | 51 |
| RT09S | TTG GAG GGG GAG GTG GGG | 126 | 100 | 52 |
| RT10S | TTG GAG GCG GTG GTG GCG | 31 | 38 | 53 |
| RT24S | TTG GAG CCG GTG GTG GCC | 40 | 57 | 54 |
| RT25S | TTG GAG GGG CTC CTC GGG | 44 | 25 | 55 |
| RT23S | TTG GAGCCG GTG GTG G | 38 | 57 | 56 |
| RT18S | GGG GTG GTG GGG | 103 | 120 | 57 |
| RT19S | G GGG TTG GGG | 30 | 89 | 58 |
| RTC07S | TG GGG | 2 | 2 | 59 |
| RTC08S | G GGG | 2 | 2 | 60 |
| RT20S | CAC TGC GGG GAG GGC TGG GG | 58 | 76 | 61 |
| RT21S | ATG GGG TGC ACA AAC TGG GG | 51 | 63 | 62 |
| RT15S | AAC GTT GAG GGG CAT | 26 | 52 | 63 |
| RT06S | TTC CAG CCC CTC CTC CCC | 29 | 22 | 64 |
| RTC06S | AAC CTC CCC CAC CAC CCC | 4 | 2 | 48 |

In preparing the data for Table 5, the in vitro activity of phosphorothioate oligonucleotides was determined by their ability to inhibit CD28 expression in anti-CD3/PMA-activated peripheral human T cells and their effect on activated IL-2 production in Jurkat T cells. Results are expressed relative to the activity of 5 μM RT03S (SEQ ID NO: 44) (100%) whose range of inhibition in 7 experiments was 52–79% of CD28 expression and 76–89% of IL-2 production. The values for the phosphodiester form of RT03D (SEQ ID NO: 49) are in parentheses.

Identification of minimal sequence which confers biological activity in vitro

Active phosphorothioate, RT03S (SEQ ID NO: 44), is an 18 mer originally designed to hybridize to the 5' untranslated region of the human CD28 gene, and has a sequence containing two sets of contiguous four G's. To identify the sequence-related factors critical for inhibition of activation-induced CD28 expression in human T cells and CD28-dependent IL-2 production in Jurkat T cells, bases were selectively added, deleted or substituted from RT03S (SEQ ID NO: 44) and activity assessed relative to the parent oligomer (Table 5). Addition of three G's at the 5' end (RT04S) or one or more changes of T to A in the region between both four G sequences (RT05S (SEQ ID NO: 51), RT09S (SEQ ID NO: 52)) did not reduce the inhibitory effect relative to RT03S (SEQ ID NO: 44). Interestingly, the sense sequence (RT11S (SEQ ID NO: 50)) also showed no change in activity relative to RT03S (SEQ ID NO: 44). However, in contrast, deletion or replacement of one or more G's by cytosine (C) within both sets of four G's (RT10S (SEQ ID NO: 53), RT24S (SEQ ID NO: 54), RT25S (SEQ ID NO: 55), RT23S (SEQ ID NO: 56) (SEQ ID NO: 56)) resulted in a marked loss of activity relative to RT03S (SEQ ID NO: 44). Deletion of the six residues 5' of the first four G's in RT03S (SEQ ID NO: 44) had no effect on the inhibitory activity of the oligonucleotide (RT18S (SEQ ID NO: 57)). In contrast, reducing (RT19S (SEQ ID NO: 58)) or increasing (RT20S (SEQ ID NO: 61), RT21S (SEQ ID NO: 62)) the number of residues between both four G sequences dramatically reduced the inhibitory activity relative to RT03S (SEQ ID NO: 44). TGGGG, GGGG or sequences containing 4 consecutive G's such as RT15S (SEQ ID NO: 63 had little or no inhibitory activity relative to RT03S (SEQ ID NO: 44). These data demonstrated that the biological activity of RT03S (SEQ ID NO: 44) is dependent on a specific sequence motif comprised of 2 sets of 4 contiguous G's separated by 3–5 residues.

In view of the tolerogenicity imparted by disrupting CD28 function (Boussiotis, V. A., Freeman, G. J., Gray, G., Gribben, J., Nadler, L. M. (1993) *J. Exp. Med.* 178, 1753–1763.), it was important to examine whether oligo-mediated inhibition of CD28 expression could provide a more effective strategy for inducing T cell anergy and alloantigen-specific tolerance in vitro. We showed that the phosphorothioate oligomers, RT03S (SEQ ID NO: 44) and RT04S, inhibited anti-CD3/PMA-induced CD28 expression in human $CD4^+$ T cells by reducing both mRNA and mature protein levels relative to oligomer dose. Furthermore, in order to demonstrate target specificity, we examined oligo-mediated effects on IL-2receptor and ICAM-1 expression: two accessory molecules known to be regulated independently of the CD28 pathway (Damle, N. K., et al., (1992) *J. Immunol.* 148, 1985–1992; June, C. H. et al., (1987) *Mol. Cell Biol.* 7, 4472–4481; Stein, C. A., et al., Y.-C. (1993) *Science* 261, 1004–1012; Boussiotis, V. A., et al., (1993) *J. Exp, Med.* 178, 1753–1763). Correspondingly, both activated message and protein levels of CD25 and surface expression of CD54 were resistant to oligomer action.

Costimulation via the CD28 pathway directly induces expression of immunomodulatory cytokines such as IL-2, IFNγ and IL-8 in activated T cells (Fraser, J. D., et al., (1991) *Science* 251, 313–316 Jenkins, M. K., et al., (1991) *J. Immunol.* 147, 2461–2466; Seder, R. A., et al., (1994) *J. Exp. Med.* 179, 299–304; Wechsler, A. S., et al., (1994) *J. Immunol.* 153, 2515–2523). For tolerogenicity to be successful, active CD28-specific oligomers must abrogate this function. Administration of active oligomers resulted in concomitant modulation of activation-induced IL-2, IFNγ and IL-8 production. To underscore the exquisite specificity of the active oligomers to inhibit CD28-dependent functions, we showed that they were unable to prevent activation-induced IL-2 production in a CD28-deficient cell line, HUT 78. Furthermore, maximal oligo-mediated inhibition of IL-8 production in activated T cells never exceeded 50% suggesting that an alternative regulatory pathway driving CD28-independent IL-8 production was preserved. Oligomer activity was not restricted to polyclonally activated T cells, as inhibition of activation-induced CD28 levels resulted in dramatically reduced T cell proliferation in both MLR and in tetanus-toxoid-specific T cell assays. Thus, our active oligomers mediated alloantigen-specific tolerance in vitro, and provide a promising alternative to the ligand capture strategy for inducing T cell hyporesponsiveness such as seen with CTLA 4 Ig, a high affinity B7 binder (Tan, P., Anasetti, C., Hansen, J. A., Melrose, J., Brunvand, M., Bradshaw, J., Ledbetter, J. A., Linsley, P. S. (1993) *J. Exp. Med.* 177, 165–173.).

In determining the duration of effect of the active pharmacophore, we observed that RT03S (SEQ ID NO: 44) showed surprisingly persistent inhibition of both activated CD28 expression and CD28-dependent T cell proliferation, even 96 h following oligomer treatment. Bioactivity was not related to toxicity as upon removal of oligomer complete reversal of inhibitory activity occurred within 24 h. Moreover, upon comparison of the phosphorothioates, RT03S (SEQ ID NO: 44) and RTC06S (SEQ ID NO: 48), our in vitro stability studies showed that secondary structure, mediated by the G-rich sequence in RT03S (SEQ ID NO: 44), increased two- to fourfold the nuclease resistance typically associated with phosphorothioates (Stein, C. A., Cheng, Y. C. (1993) *Science* 261, 1004–1012.). The extended half life (96 h) of $^{32}$P-RT03S (SEQ ID NO: 44) correlated with its duration of bioactivity. In addition, RT03D, the phosphodiester counterpart of RT03S (SEQ ID NO: 44), exhibited both reduced in vitro stability and bioactivity, an observation which is consistent with previous reports (Maltese, J.-Y., Sharma, H. W., Vassilev, L., Narayanan, R. (1995) *Nucleic Acids Res.* 23, 1146–1151). Therefore, stability imparted by secondary structure is not solely responsible for the increased bioactivity of RT03S (SEQ ID NO: 44). Thus the nuclease stability granted by both phosphorothioate modification and secondary structure may account for the prolonged inhibitory activity of RT03S (SEQ ID NO: 44).

Single base pair substitution in hybridization-dependent, antisense and antigene models can virtually abolish activity (Maltese, J.-Y., Sharma, H. W., Vassilev, L., Narayanan, R. (1995) *Nucleic Acids Res.* 23, 1146–1151.). In contrast, activity of CD28-specific oligomers was only dramatically reduced if sequential substitution occurred within both sets of four G's implying defined structural requirement for oligomer function. In addition, following cationic stabilization (100 mM KCl and NaCl) of the secondary structure present in RT03S (SEQ ID NO: 44), the oligomer melting curve showed a transition profile (data not shown) which is suggestive of G-quartet formation (Hardin, C. C., Watson, T., Corregan, M., Bailey, C. (1992) *Biochemistry* 31, 833–841). Taken together, our data provide evidence that this class of CD28-specific oligomers act via a hybridization-independent mechanism and that secondary structure of the sequence, possibly through G-quartet formation, delimits oligomer activity. Similarly, Bennett, C. F., Chiang, M. Y., Wilson-Lingardo, L., Wyatt, J. R. (1994) *Nucleic Acids Res.* 22, 3202–3209, demonstrated that activity of their phosphorothioate oligomers was based on possible G-quartet formation in sequences containing two sets of three or more consecutive G and this suggested that oligo-mediated regulation of human phospholipase $A_2$ was through specific nucleic acid-protein interaction.

Specific protein recognition by a range of G-quartet structures have been demonstrated in telomeres, centromeres (Blackburn, E. H. (1990) *J. Biol. Chem.* 265, 5919–5921), immunoglobulin switch regions (Shimizu, A., Honjo, T. (1984) *Cell* 36, 801–803) and a class of regulatory oligomers called aptamers (Bock. L. C., Griffin, L. C., Latham, J. A., Vermaas, E. H., Toole, J. J. (1992) *Nature* 355, 564–566; Huizenga, D. E., Szostak, J. W. (1995) *Biochemistry* 34, 656–665; Bergan, R., Connell, Y., Fahmy, B., Kyle, E., Neckers, L. (1994) *Nucleic Acids Res.* 22, 2150–2154). In our studies, oligomers capable of forming an intermolecular four stranded G-quartet structure from a set of four contiguous G's, such as those in telomeres (Smith, F. W., Feigon, J. (1992) *Nature* 356, 164–167), weakly inhibited CD28 expression. An example of this was RT15S (SEQ ID NO: 63, whose G-rich sequence was previously shown by others to inhibit c-myc expression (sequence 14 in Burgess, T. L., Fisher, E. F., Ross, S. L., Bready, J. V., Qian, Y.-X., Bayewitch, L. A., Cohen, A. M., Herrera, C. J., Hu, S. S.-F., Kramer, T. B., Lott, F. D., Martin, F. H., Pierce, G. F., Simonet, L., Farrell, C. L. (1995) *Proc. Natl. Acad. Sci. USA* 92, 4051–4055). Another G-rich structure, the intramolecular G-quartet, has been shown to mediate aptameric inhibition of thrombin (Wang, K. Y., McCurdy, S., Shea, R. G., Swaminanthan, S., Bolton, P. H. (1993) *Biochemistry* 32, 1989–1904; Macaya, R. F., Schultze, P., Smith, F. W., Roe, J. A., Feigon, J. (1993) *Proc. Natl. Acad. Sci. USA* 90, 3745–3749). Sequential analysis of RT03S (SEQ ID NO: 44) predicts that paired G's of residues 3–4, 7–8, 12–13 and 16–17 can potentially form such a G-quartet structure. However, removal of residues 1–6 (RT18S (SEQ ID NO: 57)), which disrupted the intramolecular quartet, was ineffective in blocking the inhibition of CD28 expression and CD28-dependent IL-2production. These data suggest that the activity of RT03S (SEQ ID NO: 44) arises from an alternate G-quartet structure.

RTO3S (SEQ ID NO: 44) indeed has a similar 12 mer sequence to a motif predicted by others (Smith, F. W., Feigon, J. (1993) *Biochemistry* 32, 8682–8692) to be essential for dimeric G-quartet formation. Dimeric G-quartets can arise from two strands of DNA, alternately parallel and antiparallel. Here, adjacent strands contribute four G's to form four stacked G-quartets. A motif on each strand, consisting of twelve residues with four bases separating two sets of contiguous four G's, was associated with formation and stability. We have shown that the core 12 mer sequence (RT18S (SEQ ID NO: 57)) has similar activity to RT03S (SEQ ID NO: 44). Also G to C substitutions (RT10S (SEQ ID NO: 53), RT23S (SEQ ID NO: 56), RT24S (SEQ ID NO: 54), RT25S (SEQ ID NO: 55)) within both the four G regions resulted in a 56–69% loss of inhibitory activity relative to RT03S (SEQ ID NO: 44). Similarly, insertion (RT20S (SEQ ID NO: 61), RT21S (SEQ ID NO: 62)) or deletion (RT19S (SEQ ID NO: 58)) of bases separating the sets of G's reduced the relative bioactivity by 52–70%. Taken together, these data suggest that a specific sequence motif, which has the capability to form a dimeric G-quartet, is critical for phosphorothioate oligo-mediated inhibition of functional CD28 expression.

The mechanism by which this type of dimeric G-quartet exerts its biological effect is unknown. However, several lines of evidence substantiate the hypothesis that this motif enables our active oligomers to function as decoys, presumably by competitively hindering the interaction of a dimeric G-quartet promoter sequence with a specific transcription factor. 1) An oligomer corresponding to an upstream region of the CD28 gene (RT11S (SEQ ID NO: 50)) exhibited equivalent biological activity to RT03S (SEQ ID NO: 44). 2) Our active oligomers function via a non-antisense mechanism. 3) These oligomers modulated CD28 mRNA expression; hence their bioactivity was not related to direct target protein interaction. 4) G-rich promoter regions are prevalent (Evans, T., Schon, E., Grazyna, G. M., Patterson, J., Efstratiadis, A. (1984) *Nucleic Acids Res.* 12, 8043–805; Kilpatrick, M. W., Torri, A., Kang, D. S., Engler, J. A., Wells, R. D. (1986) *J. Biol. Chem.* 261, 11350–11354; Clark, S. P., Lewis, C. D., Felsenfeld, G., (1990) *Nucleic Acids Res.* 18, 5119–5126.), increasing the possibility that G-quartet-forming promoter sequences are a general regulatory phenomena. 5) Double stranded oligomers can act as decoys for the transcription factor, E2F (Morishita, R., Gibbons, G. H., Horuchi, M., Ellison, K. E., Nakajima, M., Zhang, L., Kaneda, Y., Ogihara, T., Dzau, V. J. (1995) *Proc. Natl. Acad. Sci. USA* 92, 5855–5859). 6) G-rich oligomers have been shown to mediate the induction of Sp1 transcription factor (Perez, J. R., Li, Y., Stein, C. A., Majumder, S., van Oorschot, A., Narayanan, R. (1994) *Proc. Natl. Acad. Sci. USA* 91, 5957–5961).

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described makes for carrying out the invention which are obvious to those skilled in the field of organic chemistry or related fields are intended to be within the scope of the following claims.

What is claimed is:

1. A method of inhibiting the expression of CD28 in a mammal comprising subcutaneously administering to said mammal an effective amount of an oligonucleotide set forth in any one of SEQ ID NOs: 1–4, wherein CD28 expression in said mammal is inhibited and wherein the expression of IL-2, gamma-interferon, or IL-8 is inhibited.

2. An oligonucleotide which reduces CD28 expression in a T-cell, said oligonucleotide comprising a nucleic acid sequence having less than 22 bases and which includes any one of SEQ ID NOs: 1–4.

3. The oligonucleotide of claim 2, wherein said nucleic acid sequence is SEQ ID NO: 1.

4. The oligonucleotide of claim 2, wherein said nucleic acid sequence is SEQ ID NO: 2.

5. The oligonucleotide of claim 2, wherein said nucleic acid sequence is SEQ ID NO: 3.

6. The oligonucleotide of claim 2, wherein said nucleic acid sequence is SEQ ID NO: 4.

* * * * *